(12) United States Patent
Reiley et al.

(10) Patent No.: US 8,734,462 B2
(45) Date of Patent: May 27, 2014

(54) SYSTEMS AND METHODS FOR THE FIXATION OR FUSION OF BONE USING COMPRESSIVE IMPLANTS

(71) Applicant: SI-Bone Inc., San Jose, CA (US)

(72) Inventors: Mark A. Reiley, Washington, DC (US); Justin Lerman, Monte Sereno, CA (US); Richard G. Mauldin, Erie, CO (US)

(73) Assignee: SI-Bone Inc., San Jose, CA (US)

( * ) Notice: Subject to any disclaimer, the term of this patent is extended or adjusted under 35 U.S.C. 154(b) by 0 days.

(21) Appl. No.: 13/786,037

(22) Filed: Mar. 5, 2013

(65) Prior Publication Data

US 2013/0184769 A1    Jul. 18, 2013

Related U.S. Application Data

(63) Continuation of application No. 12/924,784, filed on Oct. 5, 2010, now Pat. No. 8,388,667, which is a continuation-in-part of application No. 11/136,141, filed on May 24, 2005, now Pat. No. 7,922,765, which is a continuation-in-part of application No. 10/914,629, filed on Aug. 9, 2004, now abandoned.

(51) Int. Cl.
    *A61B 17/58*    (2006.01)
    *A61B 17/60*    (2006.01)
    *A61F 2/00*     (2006.01)

(52) U.S. Cl.
    USPC .......................... 606/105; 606/300; 606/304

(58) Field of Classification Search
    USPC ............... 606/246–248, 300–321, 95, 96, 99, 606/104, 105, 279; 623/17.11–17.16; 128/898
    See application file for complete search history.

(56) References Cited

U.S. PATENT DOCUMENTS 1,951,278 A    3/1934   Ericsson
2,136,471 A   11/1938   Schneider
(Continued)

FOREIGN PATENT DOCUMENTS

EP    1287796 A1    3/2003
JP    05-176942 A   7/1993
(Continued)

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.

(Continued)

*Primary Examiner* — Mary Hoffman
*Assistant Examiner* — Christina NegrelliRodriguez
(74) *Attorney, Agent, or Firm* — Shay Glenn LLP

(57) ABSTRACT

First and second bone segments separated by a fracture line or joint can be fixated or fused by creating an insertion path through the first bone segment, through the fracture line or joint, and into the second bone segment. An anchor body is introduced through the insertion path. The distal end of the anchor body is anchored in the interior region of the second bone segment. An elongated implant structure is passed over the anchor body to span the fracture line or joint between the bone segments. The proximal end of the anchor body is anchored to an exterior region of the first bone segment to place, in concert with the anchored distal end, the anchor body in compression, to thereby compress and fixate the bone segments relative to the fracture line or joint.

30 Claims, 23 Drawing Sheets

(56) References Cited

U.S. PATENT DOCUMENTS

| | | | |
|---|---|---|---|
| 2,243,717 A | 5/1941 | Moreira |
| 2,414,882 A | 7/1947 | Longfellow |
| 2,675,801 A | 4/1954 | Bambara et al. |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 4,341,206 A | 7/1982 | Perrett et al. |
| 4,344,190 A | 8/1982 | Lee et al. |
| 4,399,813 A | 8/1983 | Barber |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,904,261 A | 2/1990 | Dove et al. |
| 4,950,270 A | 8/1990 | Bowman et al. |
| 4,961,740 A | 10/1990 | Ray et al. |
| 5,034,011 A | 7/1991 | Howland |
| 5,035,697 A | 7/1991 | Frigg |
| 5,053,035 A | 10/1991 | McClaren |
| 5,066,296 A | 11/1991 | Chapman et al. |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,443,466 A | 8/1995 | Shah |
| 5,470,334 A | 11/1995 | Ross et al. |
| 5,480,402 A | 1/1996 | Kim |
| 5,569,249 A | 10/1996 | James et al. |
| 5,593,409 A | 1/1997 | Michelson |
| 5,609,636 A | 3/1997 | Kohrs et al. |
| 5,626,616 A | 5/1997 | Speece |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,713,904 A | 2/1998 | Errico et al. |
| 5,716,358 A | 2/1998 | Ochoa et al. |
| 5,743,912 A | 4/1998 | LaHille et al. |
| 5,788,699 A | 8/1998 | Bobst et al. |
| 5,800,440 A | 9/1998 | Stead |
| 5,868,749 A | 2/1999 | Reed |
| 5,928,239 A | 7/1999 | Mirza |
| 6,010,507 A | 1/2000 | Rudloff |
| 6,053,916 A | 4/2000 | Moore |
| 6,056,749 A | 5/2000 | Kuslich |
| 6,096,080 A | 8/2000 | Nicholson et al. |
| 6,120,504 A | 9/2000 | Brumback et al. |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,270,528 B1 | 8/2001 | McKay |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,409,768 B1 | 6/2002 | Tepic et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,723,099 B1 | 4/2004 | Goshert |
| 6,740,118 B2 | 5/2004 | Eisermann et al. |
| 6,743,257 B2 | 6/2004 | Castro |
| 7,118,579 B2 | 10/2006 | Michelson |
| 7,175,663 B1 | 2/2007 | Stone |
| 7,211,085 B2 | 5/2007 | Michelson |
| 7,223,269 B2 | 5/2007 | Chappuis |
| 7,335,205 B2 | 2/2008 | Aeschlimann et al. |
| 7,452,359 B1 | 11/2008 | Michelson |
| 7,452,369 B2 | 11/2008 | Barry |
| 7,481,831 B2 | 1/2009 | Bonutti |
| 7,534,254 B1 | 5/2009 | Michelson |
| 7,569,054 B2 | 8/2009 | Michelson |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,758,646 B2 | 7/2010 | Khandkar et al. |
| 7,850,732 B2 | 12/2010 | Heinz |
| 7,857,832 B2 * | 12/2010 | Culbert et al. ............... 606/246 |
| 7,887,565 B2 | 2/2011 | Michelson |
| 7,909,832 B2 | 3/2011 | Michelson |
| 7,922,765 B2 | 4/2011 | Reiley |
| 7,942,879 B2 | 5/2011 | Christie et al. |
| 8,066,705 B2 | 11/2011 | Michelson |
| 8,066,709 B2 | 11/2011 | Michelson |
| 8,080,046 B2 * | 12/2011 | Suddaby ....................... 606/324 |
| 8,202,305 B2 | 6/2012 | Reiley |
| 8,308,779 B2 | 11/2012 | Reiley |
| 8,388,667 B2 | 3/2013 | Reiley et al. |
| 8,414,648 B2 | 4/2013 | Reiley |
| 8,425,570 B2 | 4/2013 | Reiley |
| 8,444,693 B2 | 5/2013 | Reiley |
| 8,470,004 B2 | 6/2013 | Reiley |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0038123 A1 | 3/2002 | Visotsky et al. |
| 2002/0049497 A1 | 4/2002 | Mason |
| 2002/0120275 A1 | 8/2002 | Schmieding et al. |
| 2002/0128652 A1 | 9/2002 | Ferree |
| 2002/0143335 A1 | 10/2002 | von Hoffmann et al. |
| 2002/0151903 A1 | 10/2002 | Takei et al. |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 * | 2/2003 | Pelo et al. ....................... 606/72 |
| 2003/0065332 A1 | 4/2003 | TenHuisen et al. |
| 2003/0074000 A1 | 4/2003 | Roth et al. |
| 2003/0083688 A1 | 5/2003 | Simonson |
| 2003/0097131 A1 | 5/2003 | Schon et al. |
| 2003/0199983 A1 | 10/2003 | Michelson |
| 2003/0233147 A1 | 12/2003 | Nicholson et al. |
| 2004/0024458 A1 | 2/2004 | Senegas et al. |
| 2004/0073216 A1 | 4/2004 | Lieberman |

(56) References Cited

U.S. PATENT DOCUMENTS

| | | |
|---|---|---|
| 2004/0073314 A1 | 4/2004 | White et al. |
| 2004/0087948 A1 | 5/2004 | Suddaby |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0147929 A1 | 7/2004 | Biedermann et al. |
| 2004/0181282 A1 | 9/2004 | Zucherman et al. |
| 2004/0225360 A1 | 11/2004 | Malone |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0107878 A1 | 5/2005 | Conchy |
| 2005/0124993 A1 | 6/2005 | Chappuis |
| 2005/0137605 A1 | 6/2005 | Assell et al. |
| 2005/0159749 A1 | 7/2005 | Levy et al. |
| 2005/0165398 A1 | 7/2005 | Reiley |
| 2005/0228384 A1 | 10/2005 | Zucherman et al. |
| 2005/0246021 A1 | 11/2005 | Ringeisen et al. |
| 2006/0036247 A1 | 2/2006 | Michelson |
| 2006/0036251 A1 | 2/2006 | Reiley |
| 2006/0054171 A1 | 3/2006 | Dall |
| 2006/0058793 A1 | 3/2006 | Michelson |
| 2006/0084986 A1 | 4/2006 | Grinberg et al. |
| 2006/0111779 A1 | 5/2006 | Petersen |
| 2006/0129247 A1 | 6/2006 | Brown et al. |
| 2006/0161163 A1 | 7/2006 | Shino |
| 2006/0241776 A1 | 10/2006 | Brown et al. |
| 2006/0293662 A1 | 12/2006 | Boyer, II et al. |
| 2007/0083265 A1 | 4/2007 | Malone |
| 2007/0093841 A1 | 4/2007 | Hoogland |
| 2007/0149976 A1 | 6/2007 | Hale et al. |
| 2007/0156241 A1 | 7/2007 | Reiley et al. |
| 2007/0156246 A1 | 7/2007 | Meswania et al. |
| 2007/0161989 A1 | 7/2007 | Heinz et al. |
| 2007/0233146 A1 | 10/2007 | Henniges et al. |
| 2007/0250166 A1 | 10/2007 | McKay |
| 2007/0270879 A1 | 11/2007 | Isaza et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0065215 A1 | 3/2008 | Reiley |
| 2008/0154374 A1 | 6/2008 | Labrom |
| 2008/0161810 A1 | 7/2008 | Melkent |
| 2008/0234758 A1 | 9/2008 | Fisher et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0306554 A1 | 12/2008 | McKinley |
| 2009/0018660 A1 | 1/2009 | Roush |
| 2009/0024174 A1 | 1/2009 | Stark |
| 2009/0036927 A1 | 2/2009 | Vestgaarden |
| 2009/0043393 A1 | 2/2009 | Duggal et al. |
| 2009/0099602 A1 | 4/2009 | Aflatoon |
| 2009/0099610 A1 | 4/2009 | Johnson et al. |
| 2009/0131986 A1 | 5/2009 | Lee et al. |
| 2009/0138053 A1 | 5/2009 | Assell et al. |
| 2009/0157119 A1* | 6/2009 | Hale .................... 606/247 |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0259261 A1 | 10/2009 | Reiley |
| 2009/0270929 A1 | 10/2009 | Suddaby |
| 2009/0287254 A1 | 11/2009 | Nayet et al. |
| 2009/0312798 A1* | 12/2009 | Varela .................... 606/247 |
| 2010/0094290 A1 | 4/2010 | Vaidya |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0145461 A1 | 6/2010 | Landry et al. |
| 2010/0191292 A1 | 7/2010 | DeMeo et al. |
| 2010/0268228 A1 | 10/2010 | Petersen |
| 2010/0280622 A1 | 11/2010 | McKinley |
| 2010/0286778 A1 | 11/2010 | Eisermann et al. |
| 2010/0331893 A1 | 12/2010 | Geist et al. |
| 2011/0009869 A1 | 1/2011 | Marino et al. |
| 2011/0022089 A1 | 1/2011 | Assell et al. |
| 2011/0040362 A1 | 2/2011 | Godara et al. |
| 2011/0046737 A1 | 2/2011 | Teisen |
| 2011/0087294 A1 | 4/2011 | Reiley |
| 2011/0118796 A1 | 5/2011 | Reiley et al. |
| 2011/0184478 A1 | 7/2011 | Reiley |
| 2011/0184518 A1 | 7/2011 | Trieu |
| 2011/0184519 A1 | 7/2011 | Trieu |
| 2011/0184520 A1 | 7/2011 | Trieu |
| 2011/0230966 A1 | 9/2011 | Trieu |
| 2011/0238181 A1 | 9/2011 | Trieu |
| 2011/0257755 A1 | 10/2011 | Bellemere et al. |
| 2011/0264229 A1 | 10/2011 | Donner |
| 2013/0131739 A1 | 5/2013 | Reiley |
| 2013/0218215 A1 | 8/2013 | Ginn et al. |
| 2013/0231746 A1 | 9/2013 | Ginn et al. |
| 2013/0253654 A1 | 9/2013 | Reiley |
| 2013/0289625 A1 | 10/2013 | Reiley |
| 2013/0296953 A1 | 11/2013 | Mauldin et al. |

FOREIGN PATENT DOCUMENTS

| | | |
|---|---|---|
| JP | 2004512895 | 4/2004 |
| JP | 2004516866 | 6/2004 |
| WO | WO02/38054 | 5/2002 |
| WO | WO03/007839 A2 | 1/2003 |
| WO | WO2004/002344 | 1/2004 |
| WO | WO2006003316 | 1/2006 |
| WO | WO2010/105196 A1 | 9/2010 |
| WO | WO 2011/110865 A2 | 9/2011 |

OTHER PUBLICATIONS

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Wise et al.; Minimally invasive sacroiliac arthrodesis, outcomes of a new technique; J Spinal Disord Tech; vol. 21; No. 8; pp. 579-584; Dec. 2008.

Reiley, Mark A.; U.S. Appl. No. 12/357,483 entitled "Systems and methods for the fixation or fusion of bone in the hand and wrist," filed Jan. 22, 2009 (abandoned).

Mauldin et al.; U.S. Appl. No. 13/791,746 entitled "Integrated implant," filed Mar. 8, 2013.

Mauldin, R. G.; U.S. Appl. No. 13/791,801 entitled "Threaded implant," filed Mar. 8, 2013.

Mauldin, R. G.; U.S. Appl. No. 13/791,837 entitled "Artificial joint," filed Mar. 8, 2013.

Mauldin, R. G.; U.S. Appl. No. 13/791,849 entitled "Revision tool and method," filed Mar. 8, 2013.

Mauldin et al.; U.S. Appl. No. 13/794,542 entitled "Tissue dilator and protector," filed Mar. 11, 2013.

Mauldin et al.; U.S. Appl. No. 13/794,580 entitled "Guide pin," filed Mar. 11, 2013.

Mauldin et al.; U.S. Appl. No. 13/794,611 entitled "Impactor," filed Mar. 11, 2013.

Reiley, Mark.; U.S. Appl. No. 13/858,814 entitled "Apparatus, systems, and methods for achieving trans-iliac lumbar fusion," filed Apr. 8, 2013.

Reiley, Mark; U.S. Appl. No. 13/867,941 entitled "Apparatus, systems, and methods for achieving anterior lumbar interbody fusion," filed Apr. 22, 2013.

* cited by examiner

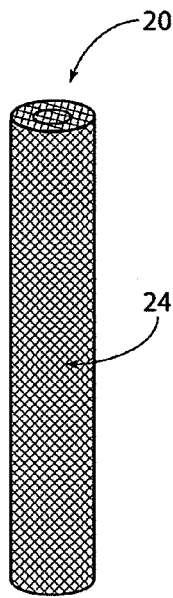 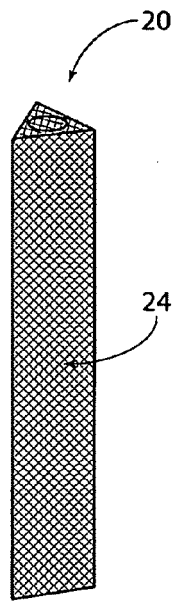 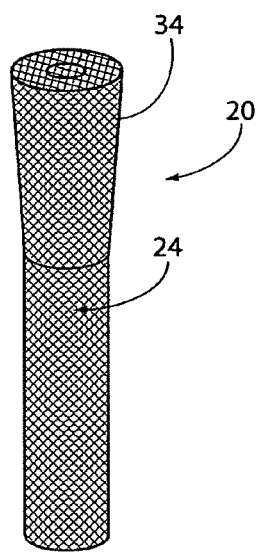
*Fig. 3*     *Fig. 4*     *Fig. 5*
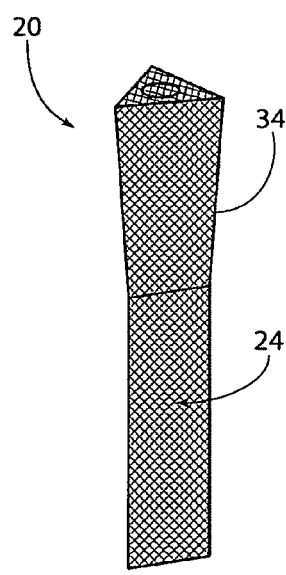 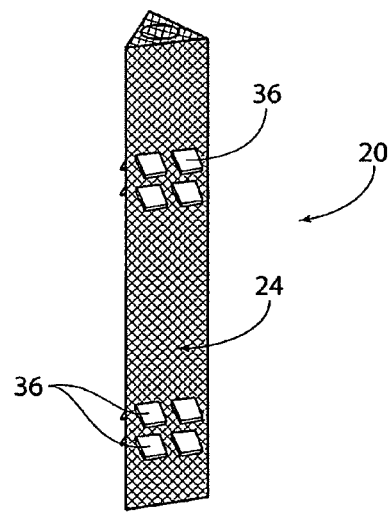
*Fig. 6*     *Fig. 7*

*(Anterior)*

*(Posterior)*

SYSTEMS AND METHODS FOR THE FIXATION OR FUSION OF BONE USING COMPRESSIVE IMPLANTS

CROSS REFERENCE TO RELATED APPLICATIONS

This application is a continuation of U.S. patent application Ser. No. 12/924,784, filed on Oct. 5, 2010, titled "SYSTEMS AND METHODS FOR THE FIXATION OR FUSION OF BONE USING COMPRESSIVE IMPLANTS," now U.S. Publication No. US-2011-0087296-A1, which is a continuation-in-part of U.S. patent application Ser. No. 11/136,141, filed on May 24, 2005, titled "SYSTEMS AND METHODS FOR THE FIXATION OR FUSION OF BONE," now U.S. Pat. No. 7,922,765 B2, which is a continuation-in-part of U.S. patent application Ser. No. 10/914,629, filed on Aug. 9, 2004, titled "SYSTEMS AND METHODS FOR THE FIXATION OR FUSION OF BONE," now U.S. Publication No. US-2006-003625-A1, now abandoned, each of which are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This application relates generally to the fixation or fusion of bone.

BACKGROUND

Many types of hardware are available both for the fixation of bones that are fractured and for the fixation of bones that are to fused (arthrodesed).

For example, the human hip girdle (see FIGS. 9 and 10) is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain.

To relieve pain generated from the SI Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screw and screw with plates are used for sacro-iliac fusion. At the same time the cartilage has to be removed from the "synovial joint" portion of the SI joint. This requires a large incision to approach the damaged, subluxed, dislocated, fractured, or degenerative joint.

SUMMARY OF THE DISCLOSURE

The invention provides bone fixation/fusion systems, devices, and related methods for stabilizing adjacent bone segments in a minimally invasive manner. The adjacent bone segments can comprise parts of the same bone that have been fractured, or two or more individual bones separated by a space or joint. As used herein, "bone segments" or "adjacent bone regions" refer to either situation, i.e., a fracture line in a single bone (which the devices serve to fixate), or a space or joint between different bone segments (which the devices serve to arthrodese or fuse). The devices can therefore serve to perform a fixation function between two or more individual bones, or a fusion function between two or more parts of the same bone, or both functions.

One aspect of the invention provides assemblies and associated methods for the fixation or fusion of bone structures comprising first and second bone segments separated by a fracture line or joint. The assemblies and associated methods comprise an anchor body sized and configured to be introduced into the first and second bone segments. The anchor body has a distal end located in an interior region of the second bone segment; a proximal end located outside an exterior region of the first bone segment; and an intermediate region spanning the fracture line or joint between the first and second bone segments. The assemblies and associated methods also include a distal anchor secured to the interior region of the second bone segment and affixed to the distal end of the anchor body to anchor the distal end in the second bone segment. The assemblies and associated methods further include a proximal anchor secured to the exterior region of the first bone segment and affixed to the proximal end of the anchor body, which, in concert with the distal anchor, places the anchor body in compression to compress and fixate the bone segments relative to the fracture line or joint. The assemblies and associated methods also include an elongated implant structure carried by the intermediate region of the anchor body and spanning the fracture line or joint between the bone segments. The elongated implant structure includes an exterior surface region treated to provide bony in-growth or through-growth along the implant structure, to accelerate the fixation or fusion of the first and second bone segments held in compression and fixated by the anchor body.

The bone fixation/fusion systems, devices, and related methods are well suited for stabilizing adjacent bone segments in the SI-Joint.

Accordingly, another aspect of the invention provides a method for the fusion of the sacral-iliac joint between an iliac and a sacrum. The method comprises creating an insertion path through the ilium, through the sacral-iliac joint, and into the sacrum. The method includes providing an anchor body sized and configured to be introduced through the insertion path laterally into the ilium and sacrum. The anchor body has a distal end sized and configured to be located in an interior region of the sacrum; a proximal end sized and configured to be located outside an exterior region of the iliac; and an intermediate region sized and configured to span the sacral-iliac joint. The method includes providing an elongated implant structure sized and configured to be passed over the anchor body to span the sacral-iliac joint between the iliac and sacrum. The elongated implant structure includes an exterior surface region treated to provide bony in-growth or through-growth along the implant structure. The method includes introducing the anchor body through the insertion path from the ilium, through the sacral-iliac joint, and into the sacrum. The method includes anchoring the distal end of the anchor body in the interior region of the sacrum. The method includes passing the elongated implant structure over the anchor body to span the sacral-iliac joint between the ilium and sacrum, and anchoring the proximal end of the anchor body to an exterior region of the ilium, which, in concert with the anchored distal end, places the anchor body in compression to compress and fixate the sacral-iliac joint. The bony in-growth or through-growth region of the implant structure accelerates the fixation or fusion of the sacral-iliac joint held in compression and fixated by the anchor body.

BRIEF DESCRIPTION OF THE DRAWINGS

FIGS. 3 to 7 are alternative embodiments of an implant structure which forms a part of the compression stem assembly shown in FIGS. 1 and 2, illustrating different cross-sectional geometries and configurations for the implant structure 20.

FIGS. 11 to 13A and 13B are anatomic views showing, respectively, in exploded perspective, assembled perspective, assembled anterior view, and assembled axial section view, the implantation of three implant structures, without association of a compression stem assembly, for the fixation of the SI-Joint using a lateral approach laterally through the ilium, the SI-Joint, and into the sacrum S1.

FIGS. 14 to 16A and 16B are anatomic views showing, respectively, in exploded perspective, assembled perspective, assembled anterior view, and assembled axial section view, the implantation of three implant structures, in association with a compression stem assembly, for the fixation of the SI-Joint using a lateral approach laterally through the ilium, the SI-Joint, and into the sacrum S1.

FIGS. 17 to 19A and 19B are anatomic views showing, respectively, in exploded perspective, assembled perspective, assembled lateral view, and assembled axial section view, the implantation of three implant structures, without association of a compression stem assembly, for the fixation of the SI-Joint using a postero-lateral approach entering from the posterior iliac spine of the ilium, angling through the SI-Joint, and terminating in the sacral alae.

FIGS. 20 to 22A and 22B are anatomic views showing, respectively, in exploded perspective, assembled perspective, assembled lateral view, and assembled axial section view, the implantation of three implant structures, in association with a compression stem assembly, for the fixation of the SI-Joint using a postero-lateral approach entering from the posterior iliac spine of the ilium, angling through the SI-Joint, and terminating in the sacral alae.

DETAILED DESCRIPTION

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

I. The Compression Stem Assembly

Figure 1:
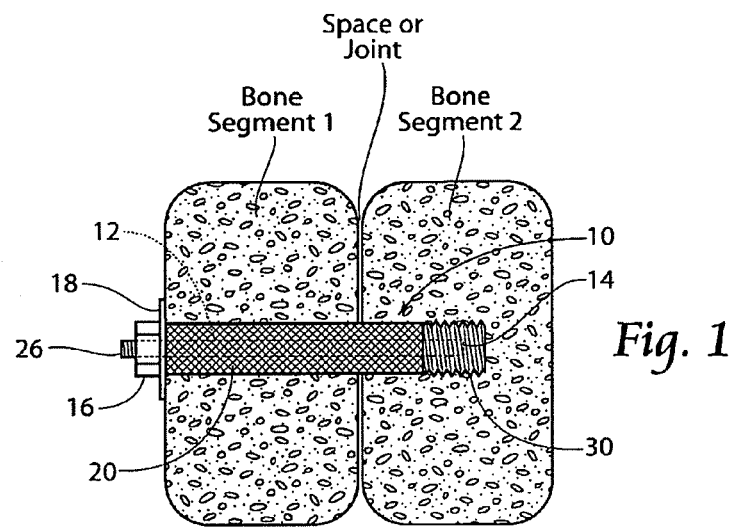
FIG. 1 is a side section view of a compression stem assembly assembled in adjacent bone regions, which are shown in FIG. 1 in a diagrammatically fashion for the purpose of illustration, without anatomic detail, which is later shown, e.g., in FIG. 16.
Figure 2:
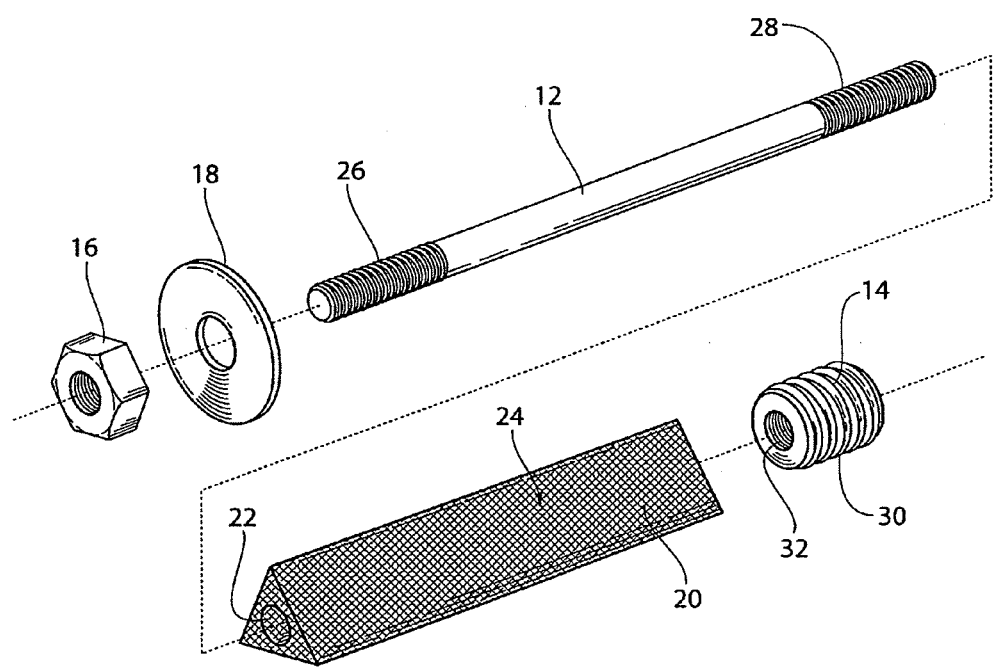
FIG. 2 is an exploded perspective view of the components of the compression stem assembly shown in FIG. 1 prior to assembly.

FIGS. 1 and 2 show in assembled and exploded views, respectively, a representative configuration of a compression stem assembly 10 sized and configured for the fixation of bone fractures (i.e., fixation of parts of the same bone) or for the fixation of bones which are to be fused (arthrodesed) (i.e. fixation of two or more individual bones that are adjacent and/or jointed). For the sake of shorthand, the assembly 10 will sometimes be called a bone fixation/fusion compression assembly, to indicate that it can perform a fixation function between two or more individual bones), or a fusion function between two or more parts of the same bone, or both functions. As used herein, "bone segments" or "adjacent bone regions" refer to either situation, i.e., a fracture line in a single bone or a space or joint between different bone segments. In FIG. 1, the bone segment or adjacent bone regions are shown diagrammatically without anatomic detail for the purpose of illustration. Later, e.g., in FIGS. 13 to 16 and FIGS. 20 to 22, the bone segments or adjacent bone regions are shown in a specific anatomic setting, comprising the joint between the sacrum and the ilium of the pelvis, also anatomically called the sacroiliac joint (SI-Joint).

As shown in FIGS. 1 and 2, the compression stem assembly 10 comprises an anchor body 12, which (as shown in FIG. 1) is sized and configured to be placed in compression within bone segments or adjacent bone regions. In a representative embodiment, the anchor body 12 takes the form of a cylindrical anchor pin or rod. Still, the anchor body 12 can possess other geometries.

The anchor body 12 is anchored at a distal end to a distal anchor screw 14 coupled to an interior bone region in one side of the space or joint. The anchor body 12 is secured at a proximal end, on the opposite side of the space or joint, to an exterior bone region by an anchor nut 16 and anchor washer 18. The distal anchor screw 14 and anchor nut 16 hold the anchor body 12 in compression and, in doing so, the anchor body 12 compresses and fixates the bone segments or adjacent bone regions.

The anchor body 12 carries within the bone regions or segments an elongated, stem-like, cannulated implant structure 20. The implant structure 20 includes an interior bore 22 that accommodates its placement by sliding over the anchor body 12. As FIG. 2 shows, the implant structure 20 includes a region 24 formed along at least a portion of its length to promote bony in-growth onto or into surface of the structure and/or bony growth entirely through all or a portion of the structure. The bony-in-growth or through-growth region 24 along the surface of the implant structure 20 accelerates bony in-growth or through-growth onto, into, or through the implant structure 20. Bony in-growth or through-growth onto, into, or through the implant structure 20 helps speed up the fusion process or fracture healing time of the bone segments or adjacent bone regions held in compression and fixated by the anchor body 12.

A. The Anchor Body, Nut, and Washer

The anchor body 12, nut 16, and washer 18 can be foamed—e.g., by machining, molding, or extrusion—from a material usable in the prosthetic arts that is capable of being placed into and holding compressive forces and that is not subject to significant bio-absorption or resorption by surrounding bone or tissue over time. The anchor body 12, nut 16, and washer 18 are intended to remain in place for a time sufficient to stabilize the fracture or fusion site. Examples of such materials include, but are not limited to, titanium, titanium alloys, tantalum, chrome cobalt, surgical steel, or any other total joint replacement metal and/or ceramic, sintered glass, artificial bone, any uncemented metal or ceramic surface, or a combination thereof.

In length (see FIG. 1), the anchor body 12 is sized to span a distance through one adjacent bone segment or region, through the intervening space or joint, and at least partially into the other adjacent bone segment or region. The anchor body 12 is sized on length and diameter according to the local anatomy. The morphology of the local structures can be generally understood by medical professionals using textbooks of human skeletal anatomy along with their knowledge of the site and its disease or injury. The physician is also able to ascertain the dimensions of the anchor body 12 based upon prior analysis of the morphology of the targeted bone region using, for example, plain film x-ray, fluoroscopic x-ray, or MRI or CT scanning. A representative diameter for the anchor body 12 can range between 3.2 mm to 3.5 mm.

As best shown in FIG. 2, at least the proximal and distal regions of the anchor body 12 include external helical ridges or screw threads 26 and 28 formed around the cylindrical body of the anchor body 12. Alternatively, the anchor body 12, if desired, can be threaded substantially along its entire length. Desirably, the direction of the screw threads 26 and 28 is the same at both proximal and distal regions of the anchor body 12, e.g., they desirably comprise right-hand threads.

The proximal region of the anchor body 12 carrying the threads 26 is sized to extend, in use, a distance outside the one adjacent bone segment or region. In this way, the proximal region is, in use, exposed so that the proximal anchor nut 16 and washer 18 can be attached. The anchor nut 16 includes complementary internal screw threads that are sized and configured to mate with the external screw threads 26 on the proximal region of the anchor body 12. Representative diameters for an anchor nut 16 and anchor washer 18 for a 3.2 mm anchor body 12 are, respectively, 3.2 mm and 8 mm.

The distal region of the anchor body 12 carrying the threads 28 is sized to extend at least partially into the other adjacent bone segment or region, where it is to be coupled to the anchor screw 14, as will next be described.

B. The Anchor Screw

Like the anchor body 12, nut and washer 18, the anchor screw 14 can likewise be formed—e.g., by machining, or molding—from a durable material usable in the prosthetic arts that is capable of being screwed into bone and that is not subject to significant bio-absorption or resorption by surrounding bone or tissue over time. The anchor screw 14, like the other components of the compression assembly 10, is intended to remain in place for a time sufficient to stabilize the fracture or fusion site. Examples of such materials include, but are not limited to, titanium, titanium alloys, tantalum, chrome cobalt, surgical steel, or any other total joint replacement metal and/or ceramic, or a combination thereof.

The anchor screw 14 is sized to span a distance within the other adjacent bone segment or region at the terminus of the threaded distal region 28 of the anchor body 12. As best shown in FIG. 2, the anchor screw 14 includes external helical ridges or screw threads 30 formed around the cylindrical body of the anchor screw 14. The external screw threads 30 are sized and configured to gain purchase in bone when rotated, so that the anchor screw 14 can be advanced and seated by rotation into bone in the bone segment or region. The anchor screw 14, seated within the bone, resists axial migration and separation. A representative range of lengths for the anchor screw 14 can be between 5 mm to 20 mm, again depending upon the demands of the local anatomy. A representative diameter for the anchor screw 14 is about 7 mm.

The anchor screw 14 also includes internal helical ridges or screw threads 32 formed within a bore in the anchor screw 14. The internal screw threads 32 are sized and configured to mate with the complementary external screw threads 28 on the distal region of the anchor body 12. When threaded and mated to the internal screw threads 32 of the anchor screw 14, the anchor screw 14 anchors the distal region of the anchor body 12 to bone to resists axial migration of the anchor body 12. As before described, the anchor screw 14 (on the distal end) and the anchor nut 16 and anchor washer 18 (on the proximal end) hold the anchor body 12 in compression, thereby compressing and fixating the bone segments or adjacent bone regions.

Alternatively, in place of the anchor screw 14, an internally threaded component free external screw threads can be is sized and configured to be securely affixed within the broached bore in the most distal bone segment where the broached bore terminates, e.g., by making an interference fit and/or otherwise being secured by the use of adhesives. Like the anchor screw 14, the interference fit and/or adhesives anchor the overall implant structure. Adhesives may also be used in combination with the anchor screw 14.

C. The Implant Structure

The implant structure 20 can be formed—e.g., by machining, molding, or extrusion—from a durable material usable in the prosthetic arts that is not subject to significant bio-absorption or resorption by surrounding bone or tissue over time. The implant structure 20, like the other components of the compression assembly 10, is intended to remain in place for a time sufficient to stabilize the fracture or fusion site. Such materials include, but are not limited to, titanium, titanium alloys, tantalum, tivanium (aluminum, vanadium, and titanium), chrome cobalt, surgical steel, or any other total joint replacement metal and/or ceramic, sintered glass, artificial bone, any uncemented metal or ceramic surface, or a combination thereof. Alternatively, the implant structure 20 may be formed from a suitable durable biologic material or a combination of metal and biologic material, such as a biocompatible bone-filling material. The implant structure 20 may be molded from a flowable biologic material, e.g., acrylic bone cement, that is cured, e.g., by UV light, to a non-flowable or solid material.

The implant structure 20 is sized according to the local anatomy. The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone region using, for example, plain film x-ray, fluoroscopic x-ray, or MRI or CT scanning.

As FIGS. 3 to 7 show, the implant structure 20 can take various shapes and have various cross-sectional geometries. The implant structure 20 can have, e.g., a generally curvilinear (i.e., round or oval) cross-section—as FIG. 3 shows for purposes of illustration—or a generally rectilinear cross section (i.e., square or rectangular or triangular—as FIG. 4 shows for purposes of illustration—or combinations thereof. In FIG. 2, the implant structure 20 is shown to be triangular in cross section, which effectively resists rotation and micromotion once implanted.

As FIGS. 5 and 6 show, the implant structure 20, whether curvilinear (FIG. 5) or rectilinear (FIG. 6) can include a tapered region 34 at least along a portion of its axial length, meaning that the width or diameter of the implant structure 20 incrementally increases along its axial length. Desirably, the tapered region 34 corresponds with, in use, the proximal region of the implant structure 20 (i.e., the last part of the implant structure 20 to enter bone). The amount of the incremental increase in width or diameter can vary. As an example, for an implant structure 20 having a normal diameter of 7 mm, the magnitude of the incremental increase at its maximum can range between about 0.25 mm to 1.25 mm. The tapered region 34 further enhances the creation and maintenance of compression between the bone segments or regions.

To further enhance the creation and maintenance of compression between the bone segments or regions (see FIG. 7), the implant structure 20, whether curvilinear or rectilinear or tapered, can include projecting bone-gripping surfaces 36 in the form of "teeth" or wings or the like. The teeth or wings 36 can project, e.g., 2 to 4 mm from the surface of the implant structure 20 and face in the direction of the compression forces at proximal and distal ends of the implant structure 20, taking purchase into the bone segments as they are compressed together by the compression assembly.

The bony in-growth or through-growth region 24 may extend along the entire outer surface of the implant structure 20, as shown in FIG. 1 or 2, or the bony in-growth or through-growth region 24 may cover just a specified distance on either side of the bone segments or fracture line. The bony in-growth region 24 or through-growth can comprise, e.g., through holes, and/or various surface patterns, and/or various surface textures, and/or pores, or combinations thereof. The configuration of the bony in-growth or through-growth region 24 can, of course, vary. By way of examples, the bony in-growth or through-growth region 24 can comprise an open mesh configuration; or beaded configuration; or a trabecular configuration; or include holes or fenestrations. Any configuration conducive to bony in-growth and/or bony through-growth will suffice.

The bony in-growth or through-growth region 24 can be coated or wrapped or surfaced treated to provide the bony in-growth or through-growth region, or it can be formed from a material that itself inherently possesses a structure conducive to bony in-growth or through-growth, such as a porous mesh, hydroxyapetite, or other porous surface. The bony in-growth or through-growth region can include holes that allow bone to grow throughout the region.

In a preferred embodiment, the bony in-growth region or through-growth region 24 comprises a porous plasma spray coating on the implant structure 20. This creates a biomechanically rigorous fixation/fusion system, designed to support reliable fixation/fusion and acute weight bearing capacity.

The bony in-growth or through-growth region 24 may further be covered with various other coatings such as antimicrobial, antithrombotic, and osteoinductive agents, or a combination thereof. The entire implant structure 20 may be impregnated with such agents, if desired.

D. Implantation of the Compression Stem Assembly

FIGS. 8A to 8L diagrammatically, show for purposes of illustration, a representative procedure for implanting a compression stem assembly 10. More detailed, anatomically-focused descriptions of particular implantation techniques of the compression stem assembly 10 in the SI-Joint will be described later.

Figure 8A:
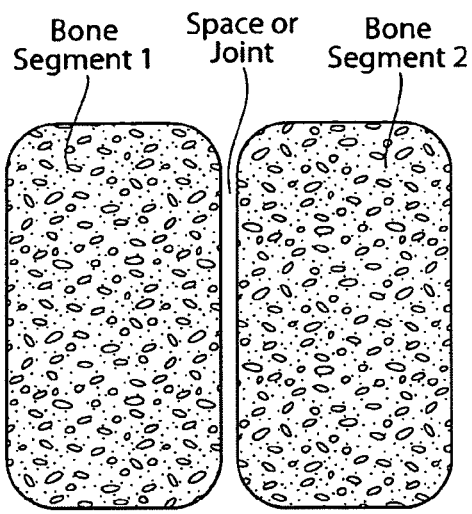
FIGS. 8A to 8L are side section views of the introduction and assembly of the compression stem assembly shown in FIGS. 1 and 2, which is shown in FIGS. 8A to 8L in a diagrammatically fashion for the purpose of illustration, without anatomic detail, as later shown, e.g., in FIG. 16.
Figure 8B:
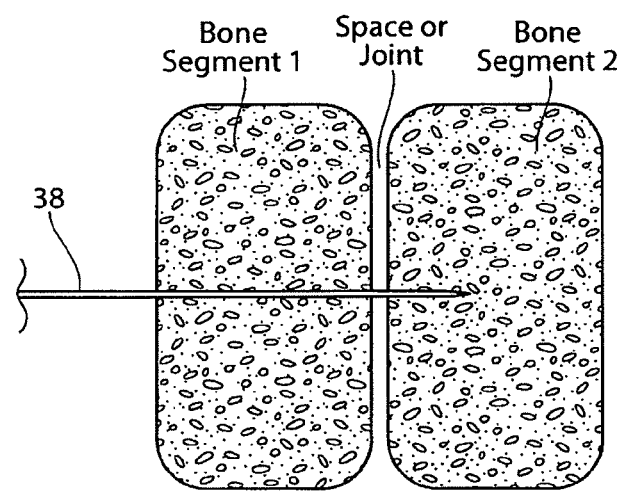

The physician identifies the bone segments or adjacent bone regions that are to be fixated or fused (arthrodesed) (see FIG. 8A). Aided by conventional visualization techniques, e.g., using X-ray image intensifiers such as a C-arms or fluoroscopes to produce a live image feed which is displayed on a TV screen, a guide pin 38 is introduced by conventional means (see FIG. 8B) through the one adjacent bone segment or region, through the intervening space or joint, and partially into the other adjacent bone segment or region.

A cannulated drill bit 40 is passed over the guide pin 38 (see FIG. 8C), to form a pilot insertion path or bore 42 through the one adjacent bone segment or region, through the intervening space or joint, and partially into the other adjacent bone segment or region. A single drill bit or multiple drill bits 40 can be employed to drill through bone fragments or bone surfaces to create a pilot bore 42 of the desired size and configuration. A region of bone distal to the pilot bore 42 is left undrilled and native for seating of the anchor screw 14. When the pilot bore 42 is completed, the cannulated drill bit 40 is removed.

A broach 44 having the external geometry and dimensions matching the external geometry and dimensions of the implant structure 20 (which, in the illustrated embodiment, is triangular) (see FIG. 8D) is tapped over the guide pin 38 through the pilot bore 42. The shaped broach 44 cuts along the edges of the pilot bore 42 to form the desired profile (which, in the illustrated embodiment, is triangular) to accommodate the implant structure 20 through the one adjacent bone segment or region, through the intervening space or joint, and partially into the other adjacent bone segment or region.

The broach 44 is withdrawn (see FIG. 8E), and the anchor screw 14 (its internal screw threads 32 mated to the distal end of a cannulated threaded screw driver 46) is passed over the guide pin 38 to the terminus of the broached bore 48 in the distal bone segment. The anchor screw 14 is threaded by operation of the screw driver 46 (see FIG. 8F) into the undrilled and native bone beyond the terminus of the broached bore 48. For example, the anchor screw 14 can be advanced and buried in bone at least 5 mm beyond the terminus of the broached bore 48.

Figure 8C:
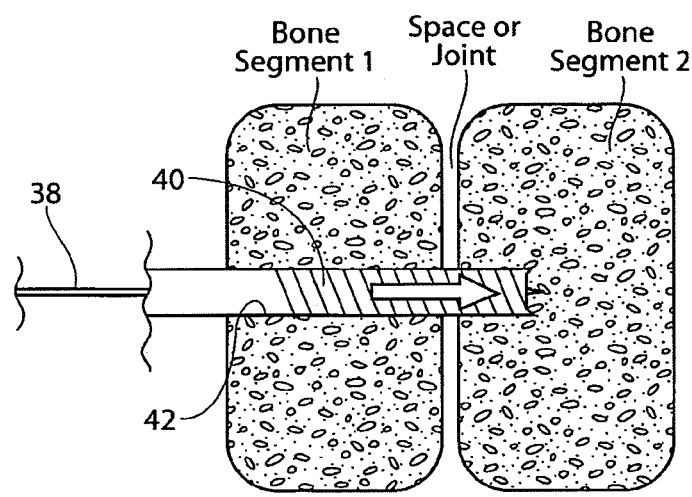
Figure 8D:
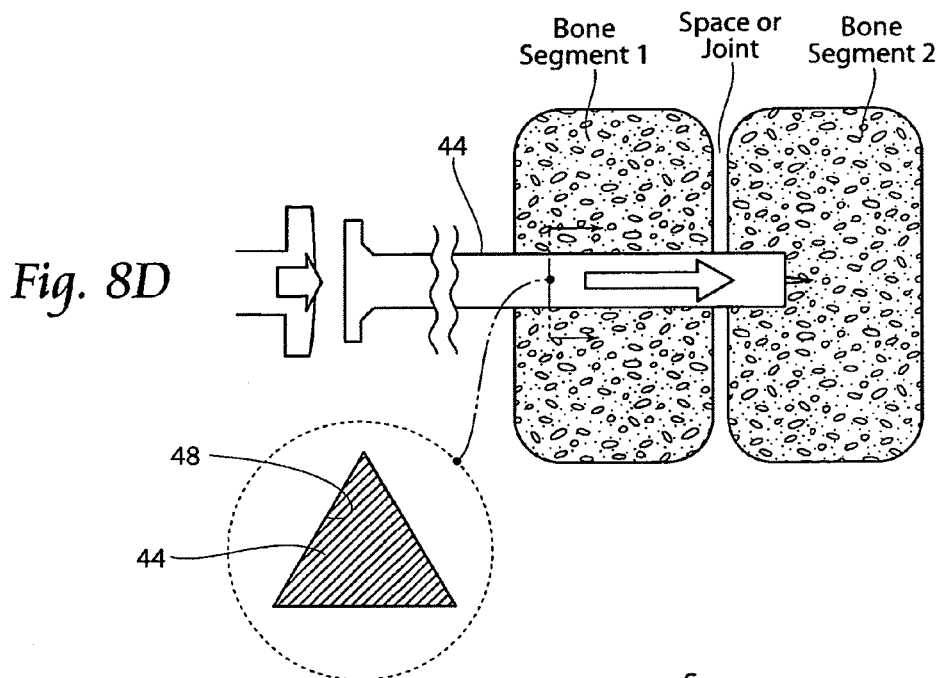
Figure 8E:
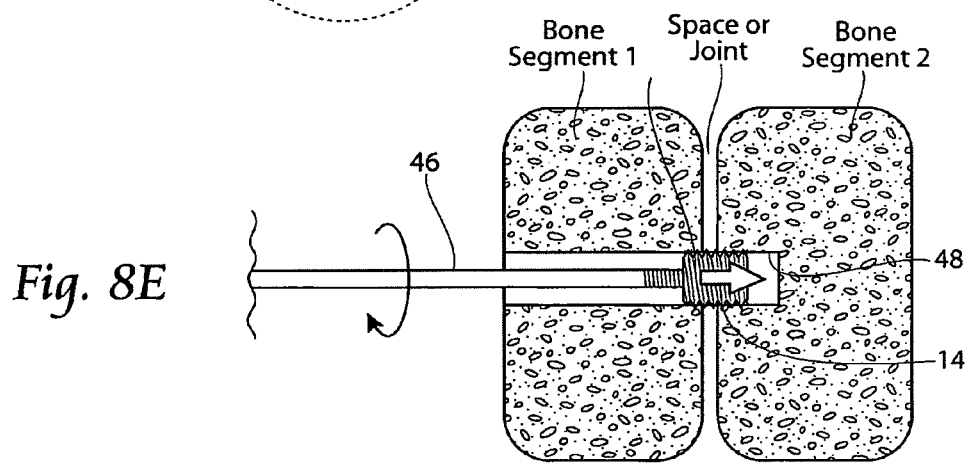
Figure 8F:
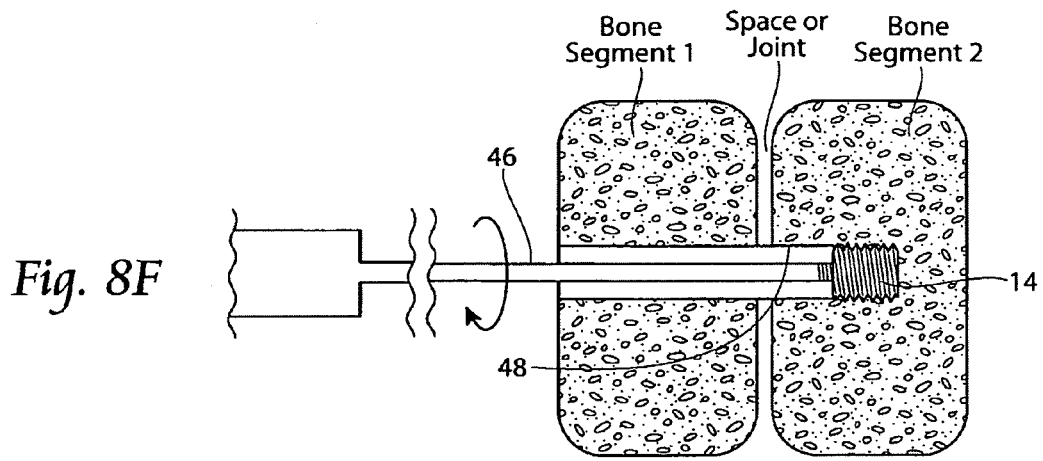
Figure 8G:
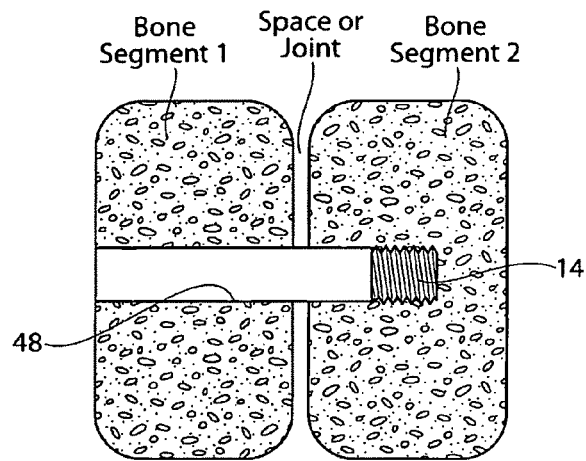

The threaded screw driver 46 is unthreaded by reverse rotation from the anchor screw 14, and the guide pin 38 is removed (see FIG. 8G). The anchor body 12 is inserted, and its threaded distal end 28 is threaded into and mated with the internal screw threads 32 of the anchor screw 14 (see FIG. 8H).

Figure 8H:
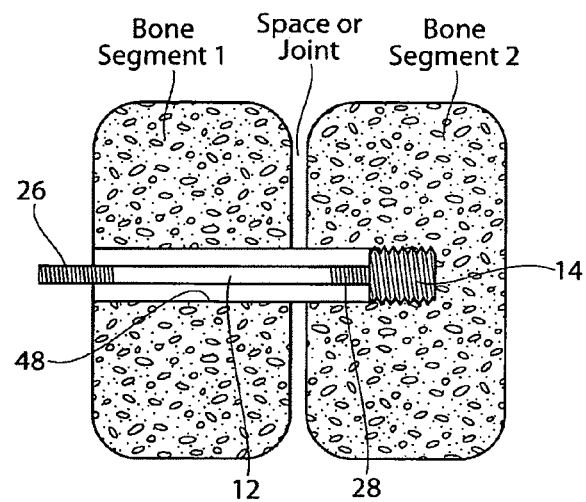

As shown in FIG. 8H, due to its purposeful size and configuration, when its threaded distal end 28 is suitably threaded to the anchor screw 14, the threaded proximal end 26 of the anchor body 12 projects an exposed distance outside the proximal end of the broached bore 48.

Figure 8I:
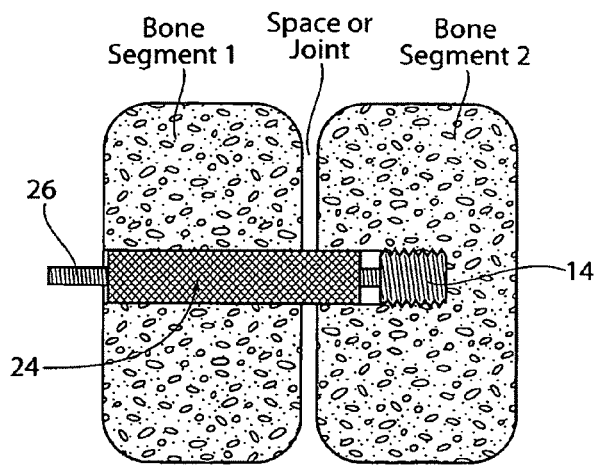

The implant structure 20 is passed over the anchor body 12 by sliding it over the anchor body 12. As FIG. 8I shows, the length of the implant structure 20 selected is less than the distance between the anchor screw 14 and the threaded proximal end 26, such that, when initially inserted and before compression is applied to the anchor body 26, the distal end of the implant structure 20 is spaced from the proximal end of the anchor screw 14 (see FIG. 8I). The distance can range, e.g., between about 4 mm to about 10 mm.

Figure 8J:
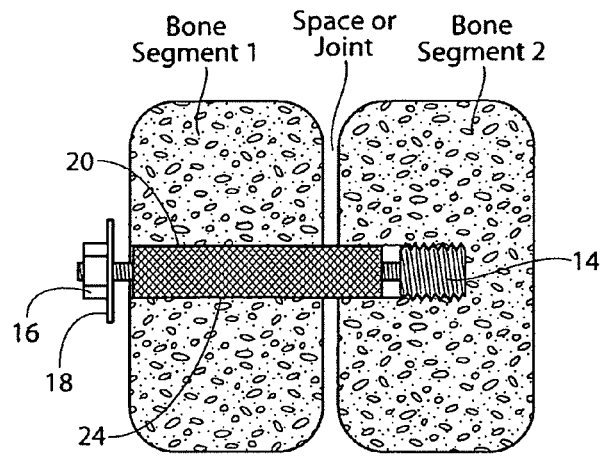
Figure 8K:
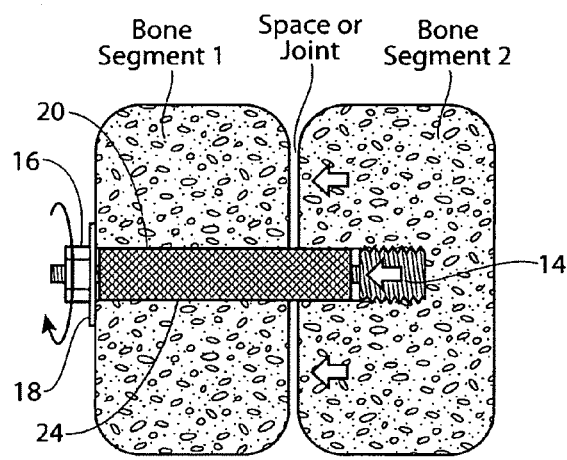
Figure 8L:
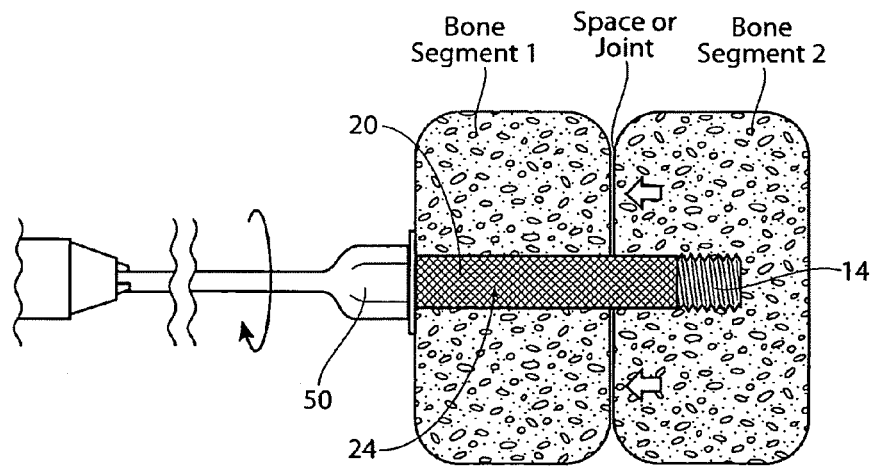

The anchor washer 18 is passed by sliding over the exposed threaded proximal end 26 of the anchor body 12 into abutment against an exterior bone surface (see FIG. 8J). The anchor nut 16 is threaded onto and mated to the threaded proximal end 26 of the anchor body 12 (see FIG. 8K). The anchor nut 16 is tightened against the anchor washer 18 using a hand (or powered) chuck 50 (see FIG. 8L), until a desired amount of compression is applied to the bone regions by the assembly 10. The compression will reduce the distance between the bone segments (as FIGS. 8K and 8L show), as the distal end 28 of the anchor body 12, affixed to the anchor screw 14 in the more distal bone segment, draws the more distal bone segment toward the more proximal bone segment, while eventually placing the implant structure 20 itself into compression within the broached bore 48 as the implant structure 20 comes into abutment against both the anchor washer 18 and the anchor screw 14, assuring intimate contact between the bony in-growth region 24 and bone within the broached bore 48.

The intimate contact created by the compression between the bony in-growth or through-growth region 24 along the surface of the implant structure 20 accelerates bony in-growth or through-growth onto, into, or through the implant structure 20, to accelerate the fusion process or fracture healing time.

As will be described in greater detail later, more than one compression stem assembly 10 can be implanted in a given bone segment. For example, as will be described later (see, e.g., FIG. 20), three such compression stem assemblies can be implanted to fuse a SI-Joint.

E. Alternative Embodiments
1. Distal Anchor Plate

Figure 31:
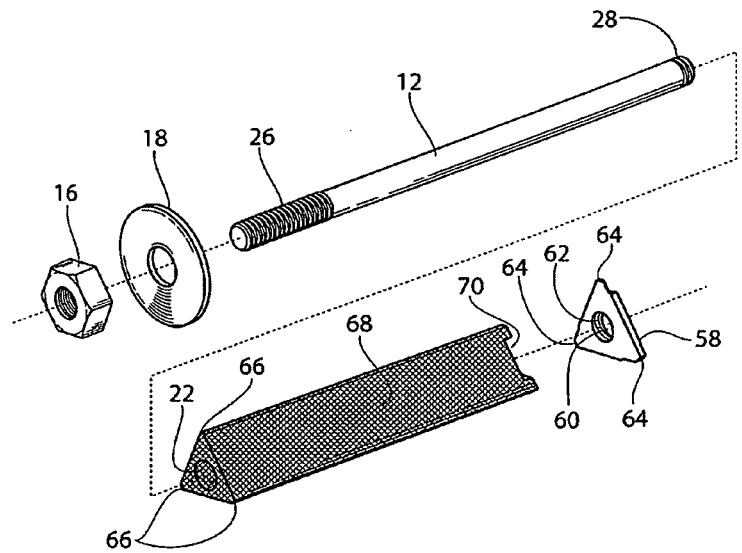
FIG. 31 is an exploded perspective view of the components of an alternative embodiment of a compression stem assembly prior to assembly.
Figure 32:
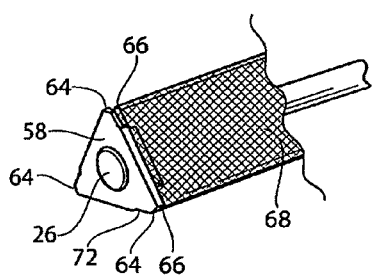
FIGS. 32 and 33 are perspective views of the alternative embodiment of a compression stem assembly shown in FIG. 31 after assembly, showing rotation of an anchor plate associated with the assembly from an aligned position (FIG. 32) to a bone-gripping position (shown in FIG. 33), to anchor the assembly in bone.
Figure 33:
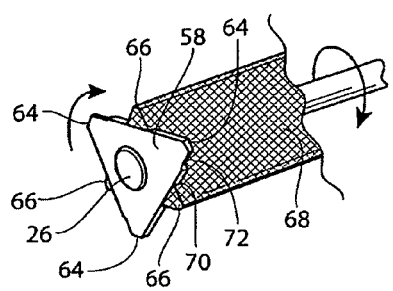

An alternative embodiment for the compression stem assembly 10 is shown in FIGS. 31 to 33. In use, the compression stem assembly 10 is sized and configured to be implanted in adjoining bone segments, which are separated by a space or joint, for the purpose of bone fixation or joint fusion, as already described.

In this embodiment (see FIG. 31), the anchor body 12, nut 16, and washer 18 are sized and configured as previously described. Likewise, the implant structure 20 is sized and configured with a generally rectilinear cross section, as also earlier described and shown in FIG. 4.

In this embodiment, instead of a threaded anchor screw 14, the distal end of the assembly 10 is anchored into bone by a generally rectilinear anchor plate 58. The anchor plate 58 is formed—e.g., by machining, or molding—from a hard, durable material usable in the prosthetic arts that is capable of cutting into and gaining purchase in bone, and that is not subject to significant bio-absorption or resorption by surrounding bone or tissue over time.

As best shown in FIGS. 31 and 32, the rectilinear anchor plate 58 is sized and configured to match the rectilinear cross section of the implant structure itself. In the illustrated arrangement, the implant structure 20 is generally triangular in cross section, and so, too, is the anchor plate 58. As such, the anchor plate 58 includes apexes 64. The sides of the anchor plate 58 between the apexes are sharpened to comprise bone cutting edges 72.

The anchor plate 58 also includes a bore 60 in its geometric center (see FIG. 31). Internal helical ridges or screw threads 62 are formed within the bore 68. The internal screw threads 62 are sized and configured to mate with the complementary external screw threads 28 on the distal region of the anchor body 12. The distal region of the anchor body 12 can thereby be threaded to the anchor plate 58 (as shown in FIG. 32). When threaded to the anchor body 12, the anchor plate 58 rotates in common with the anchor body 12 (as shown in FIG. 33).

Prior to introduction of the implant structure 20 into the broached bore 48 formed in the manner previously described (and as shown in FIGS. 8A to 8D), the anchor body 12 is passed through the bore 22 of the implant structure 20, and the anchor plate 58 is threaded to the distal threaded region 26 of the anchor body 12, which is sized to project beyond the distal end of the implant structure 20. Further, as FIG. 32 shows, the anchor plate 58 is additionally rotationally oriented in a position aligned with the distal end of the implant structure 20. In the aligned position (FIG. 32), the apexes 64 of the anchor plate 58 overlay and register with the apexes 66 of the distal end of the implant structure 20. The implant structure 20, anchor body 12, and anchor plate 58 are introduced as a unit through the broached bore 48 in the orientation shown in FIG. 32. In the aligned position, the anchor plate 58 offers no resistance to passage of the implant structure 20 through the broached bore 48.

Upon contacting the terminus of the broached bore, the proximal end of the anchor body 58 is rotated 60.degree. degrees (as shown in FIG. 33). The rotation moves the anchor plate 58 into an extended, bone-gripping position not longer aligned with the distal end of the implant structure 20 (as is shown in FIG. 33). In the extended, bone-gripping position, the apexes 64 of the triangular anchor plate 58 project radially outward from the triangular sides 68 of the implant structure 20. The anchor plate 58 presents at the distal end of the implant structure 20 an enlarged lateral surface area, larger than the cross sectional area of the implant structure itself.

Figure 34:
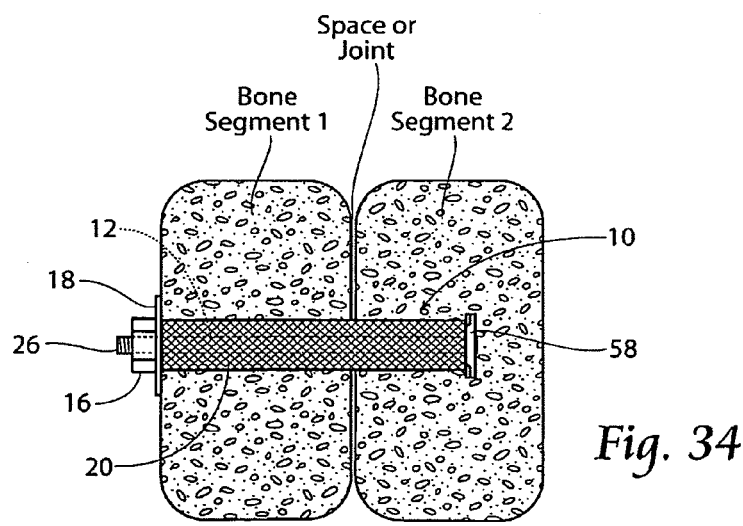
FIG. 34 is a side section view of the compression stem assembly shown in FIG. 31 assembled in adjacent bone regions, which are shown in FIG. 34 in a diagrammatically fashion for the purpose of illustration, without anatomic detail.

During rotation of the anchor plate 58 toward the bone-gripping position, the cutting edges 72 of the anchor plate 58 advance into bone and cut bone, seating the anchor plate 58 into bone in the bone segment or region (see FIG. 34). In the bone-gripping position, the anchor plate 58 anchors the distal end of the anchor body 12 into bone. The anchor plate 58 resists axial migration and separation, in much the same fashion as the anchor screw 14.

The sides 68 of the implant structure 20 at the distal end of the structure 20 preferably include cut-outs 70 (see FIGS. 31 and 32). The cut-outs 70 are sized and configured so that, when the anchor plate 58 is rotated into its bone-gripping position, the body of the anchor plate 58 adjoining the apexes detents and comes to rest within the cut outs 70, as FIG. 33 shows. Nested within the cut-outs 70, further tightening of the anchor nut 16 and washer 18 at the proximal end of the anchor body 12, as previously described, locks the anchor plate 58 in the bone-gripping, anchored position. By tightening the anchor nut, the more distal end of the anchor body 12, anchored by the plate 58 in the second bone segment, draws the second bone segment toward the first bone segment, reducing the space or joint between them, while eventually compressing the implant structure 20 between the distal anchor plate 58 and the proximal nut/washer (as FIG. 34 shows), thereby comprising a compression stem assembly 10.

2. Two Piece Compressible Implant Structure

Figure 35A:
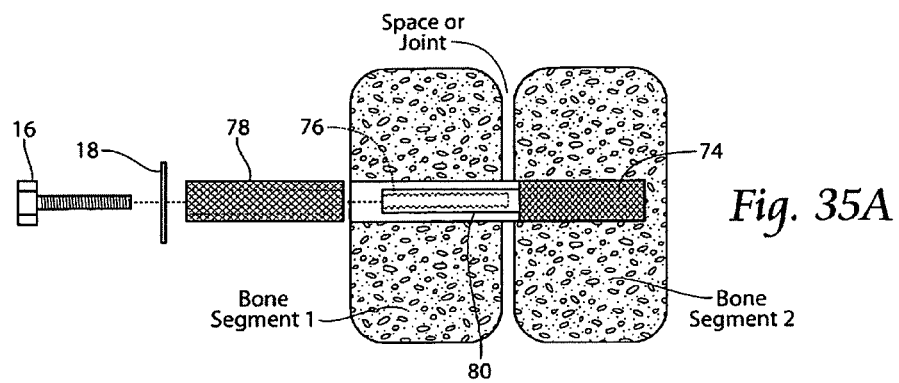
FIGS. 35A and 35B are side section views of an alternative embodiment of a compression stem assembly prior to assembly (FIG. 35A) and after assembly (FIG. 35B) in adjacent bone regions, which are shown in FIGS. 35A and 35B in a diagrammatically fashion for the purpose of illustration, without anatomic detail.
Figure 35B:
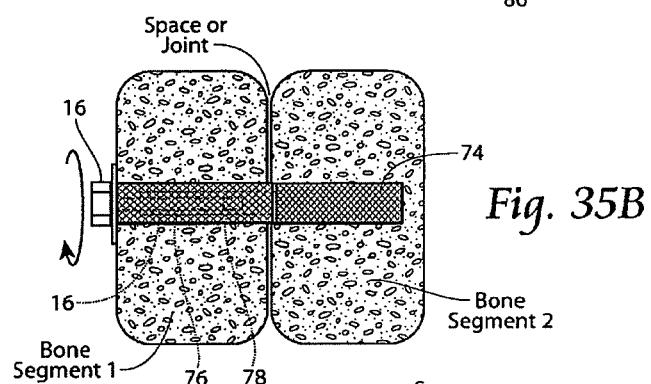

An alternative embodiment of a compressible implant structure is shown in FIGS. 35A and 35B. In use, the implant structure is sized and configured to be implanted in adjoining bone segments, which are separated by a space or joint, for the purpose of bone fixation or joint fusion, as already described.

In this embodiment (see FIG. 35A), the implant structure can possess a circular or curvilinear cross section, as previously described. Unlike previous implant structures, the implant structure 20 shown in FIG. 35A comprises two mating implant components 74 and 78.

As before described, each implant component 74 and can be formed—e.g., by machining, molding, or extrusion—from a durable material usable in the prosthetic arts that is not subject to significant bio-absorption or resorption by surrounding bone or tissue over time.

Each implant component 74 and 78 includes exterior bony in-growth or through-growth regions, as previously described.

Prior to introduction of the implant structure, a broached bore is formed through the bone segments in the manner previously described, and is shown in FIGS. 8A to 8D. The implant component 74 is sized and configured to be securely affixed within the broached bore in the most distal bone segment where the broached bore terminates, e.g., by making an interference fit and/or otherwise being secured by the use of adhesives. The implant component 74 is intended to anchor the overall implant structure.

The implant component 74 further includes a post 76 that extends through the broached bore into the most proximal bone segment, where the broached bore originates. The post 76 includes internal threads 80.

The second implant component 78 is sized and configured to be introduced into the broached bore of the most proximal bone segment. The second implant component includes an interior bore, so that the implant component 78 is installed by sliding it over the post 76 of the first implant component 74, as FIG. 35B shows.

An anchor screw 16 (desirably with a washer 18) includes external screw threads, which are sized and configured to mate with the complementary internal screw threads 80 within the post 76. Tightening the anchor screw 16 draws the first and second implant components 74 and 78 together, reducing the space or joint between the first and second bone segments and putting the resulting implant structure into compression, as FIG. 35B shows.

3. Radial Compression (Split Implant Structure)

Figure 36A:
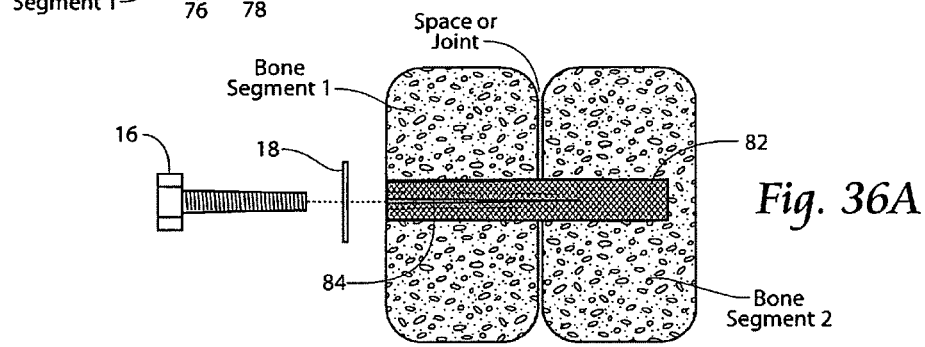
FIGS. 36A and 36B are side section views of a radially compressible implant prior to assembly (FIG. 36A) and after assembly (FIG. 36B) in adjacent bone regions, which are shown in FIGS. 36A and 36B in a diagrammatically fashion for the purpose of illustration, without anatomic detail.
Figure 36B:
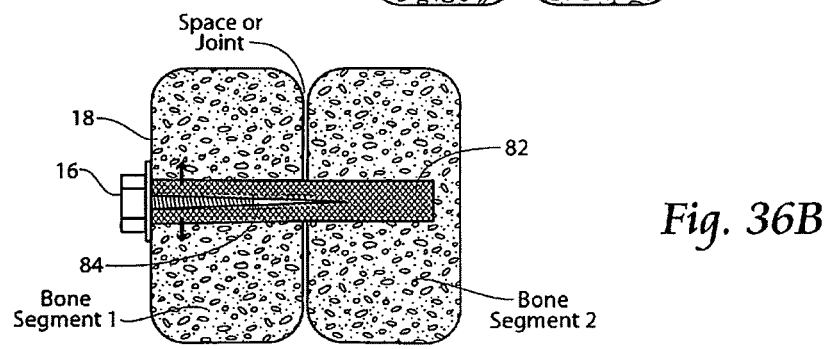

An alternative embodiment of an implant structure 82 is shown in FIGS. 36A and 36B. In use, the implant structure 82 is sized and configured to be implanted in adjoining bone segments, which are separated by a space or joint, for the purpose of bone fixation or joint fusion, as already described. The implant structure 82 is sized and configured to be placed into radial compression.

The implant structure 82 includes a body that can possess a circular or curvilinear cross section, as previously described. As before described, the implant structure 82 can be formed—e.g., by machining, molding, or extrusion—from a durable material usable in the prosthetic arts that is not subject to significant bio-absorption or resorption by surrounding bone or tissue over time.

The implant structure 82 includes one or more exterior bony in-growth or through-growth regions, as previously described.

Unlike previously described implant structures, the proximal end of the implant structure 82 includes an axial region of weakness comprising a split 84. Further included is a self-tapping screw 16. The screw 16 includes a tapered threaded body. The tapered body forms a wedge of increasing diameter in the direction toward the head of the screw 16. The screw 16 is self-tapping, being sized and configured to be progressively advanced when rotated into the split 84, while creating its own thread, as FIG. 36B shows.

Prior to introduction of the implant structure 84, a broached bore is formed through the bone segments in the manner previously described, and as shown in FIGS. 8A to 8D. The implant structure 84 is introduced into the broached bore, as FIG. 36A shows. The implant structure is desirably sized and configured to be securely affixed within the broached bore in the most distal bone segment where the broached bore terminates, e.g., by making an interference fit and/or otherwise being secured by the use of adhesives. The interference fit and/or adhesives anchor the overall implant structure 84.

After introduction of the implant structure 84 into the broached bore, the self-tapping screw 16 (desirably with a washer 18) is progressively advanced by rotation into the split 84. The wedge-shape of the threaded body of the screw 16 progressively urges the body of the implant structure 84 to expand axially outward along the split 84, as FIG. 36B shows. The expansion of the diameter of the body of the implant structure 82 about the split 84 presses the proximal end of the implant structure 82 into intimate contact against adjacent bone. The radial expansion of the body of the implant structure 82 about the split 84 radially compresses the proximal end of the implant structure 82 against bone. The radial compression assures intimate contact between the bony in-growth region and bone within the broached bore, as well as resists both rotational and axial migration of the implant structure 82 within the bone segments.

F. Implant Structures Without Compression

It should be appreciated that an elongated, stem-like, implant structure 20 having a bony in-growth and/or through-growth region, like that shown in FIG. 2, can be sized and configured for the fixation of bone fractures (i.e., fixation of parts of the same bone) or for the fixation of bones which are to be fused (arthrodesed) throughout the body without association with a compression stem assembly 10 as just described, or without other means for achieving compression of the implant structure as just described. The configuration and use of representative elongated, stem-like, implant structures 20 having bony in-growth and/or through-growth regions 24 for the fixation of bone fractures (i.e., fixation of parts of the same bone) or for the fixation of bones which are to be fused, without association with a compression stem assembly 10, are described, e.g., in U.S. patent application Ser. No. 11/136,141, filed on May 24, 2005, titled "SYSTEMS AND METHODS FOR THE FIXATION OR FUSION OF BONE," now U.S. Pat. No. 7,922,765 B2, which is incorporated herein by reference.

II. Arthrodesis of the Sacroiliac Joint Using the Implant Structures

Figure 9:
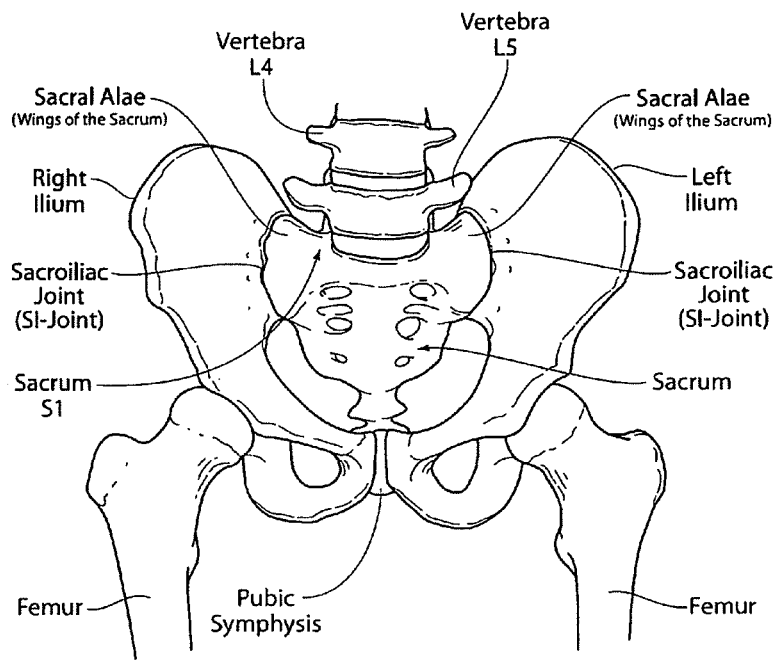
FIGS. 9 and 10 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 10:
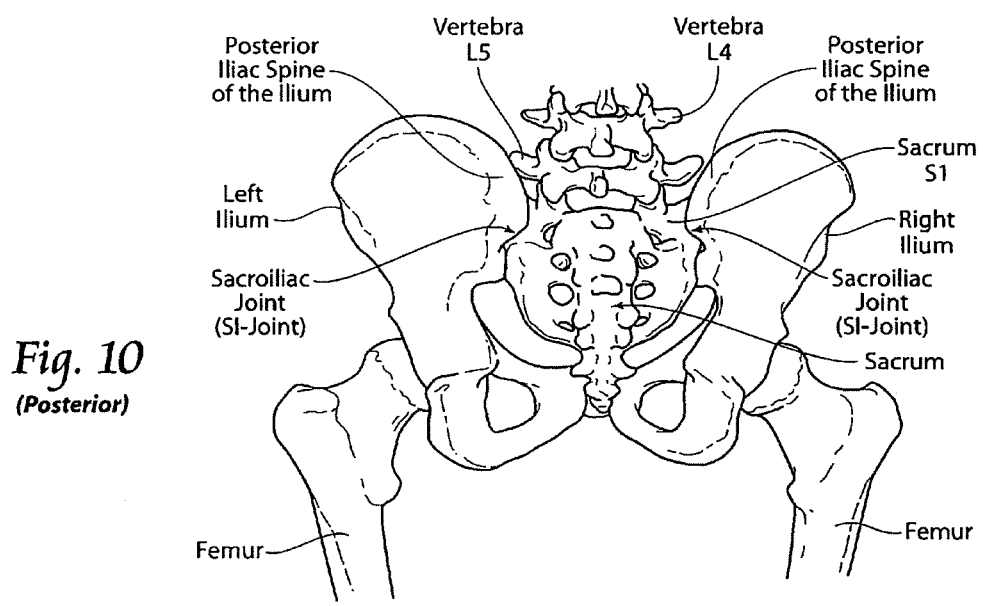

Elongated, stem-like implant structures 20 like that shown in FIG. 2 (and the alternative embodiments) make possible the fixation of the SI-Joint (shown in anterior and posterior views, respectively, in FIGS. 9 and 10) in a minimally invasive manner, with or without association with a compression stem assembly 10. These implant structures 20 can be effectively implanted through the use of two alternative surgical approaches; namely, (i) a Lateral Approach, or (ii) a Postero-Lateral Approach. Either procedure is desirably aided by conventional lateral and/or anterior-posterior (A-P) visualization techniques, e.g., using X-ray image intensifiers such as a C-arms or fluoroscopes to produce a live image feed which is displayed on a TV screen.

A. The Lateral Approach

1. Without Association of a Compression Stem Assembly

In one embodiment of a lateral approach (see FIGS. 11, 12, and 13A/B), one or more implant structures 20 are introduced (without use of a compression stem assembly 10) laterally through the ilium, the SI-Joint, and into the sacrum 51. This path and resulting placement of the implant structures 20 are best shown in FIGS. 12 and 13A/B. In the illustrated embodiment, three implant structures 20 are placed in this manner. Also in the illustrated embodiment, the implant structures 20 are triangular in cross section, but it should be appreciated that implant structures 20 of other cross sections as previously described can be used.

Before undertaking a lateral implantation procedure, the physician identifies the SI-Joint segments that are to be fixated or fused (arthrodesed) using, e.g., the Faber Test, or CT-guided injection, or X-ray/MRI of SI Joint.

Aided by lateral and anterior-posterior (A-P) c-arms, and with the patient lying in a prone position (on their stomach), the physician aligns the greater sciatic notches (using lateral visualization) to provide a true lateral position. A 3 cm incision is made starting aligned with the posterior cortex of the sacral canal, followed by blood-tissue separation to the ilium. From the lateral view, the guide pin 38 (with sleeve) (e.g., a Steinmann Pin) is started resting on the ilium at a position inferior to the sacrum S1 end plate and just anterior to the sacral canal. In A-P and lateral views, the guide pin 38 should be parallel to the S1 end plate at a shallow angle anterior (e.g., 15.degree. to 20.degree. off horizontal, as FIG. 13A shows). In a lateral view, the guide pin 38 should be posterior to the sacrum anterior wall. In the A-P view, the guide pin 38 should be superior to the S1 inferior foramen and lateral of mid-line. This corresponds generally to the sequence shown diagrammatically in FIGS. 8A and 8B. A soft tissue protector (not shown) is desirably slipped over the guide pin 38 and firmly against the ilium before removing the guide pin 38 sleeve.

Over the guide pin 38 (and through the soft tissue protector), the pilot bore 42 is drilled in the manner previously described, as is diagrammatically shown in FIG. 8C. The pilot bore 42 extends through the ilium, through the SI-Joint, and into the S1. The drill bit 40 is removed.

The shaped broach 44 is tapped into the pilot bore 42 over the guide pin 38 (and through the soft tissue protector) to create a broached bore 48 with the desired profile for the implant structure 20, which, in the illustrated embodiment, is triangular. This generally corresponds to the sequence shown diagrammatically in FIG. 8D. The triangular profile of the broached bore 48 is also shown in FIG. 11.

Figure 11:
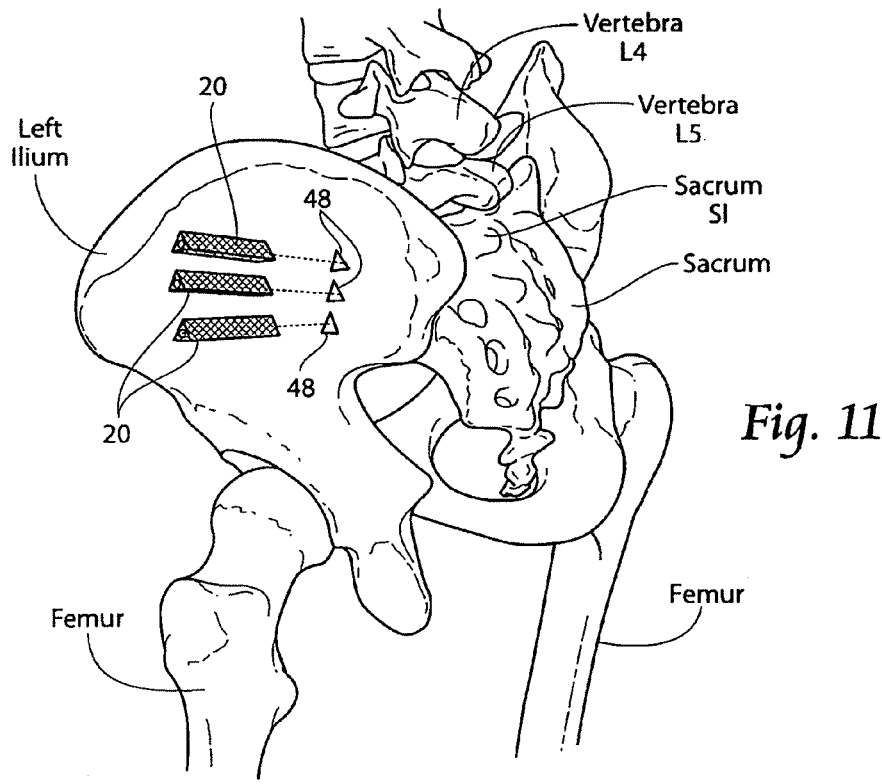
Figure 12:
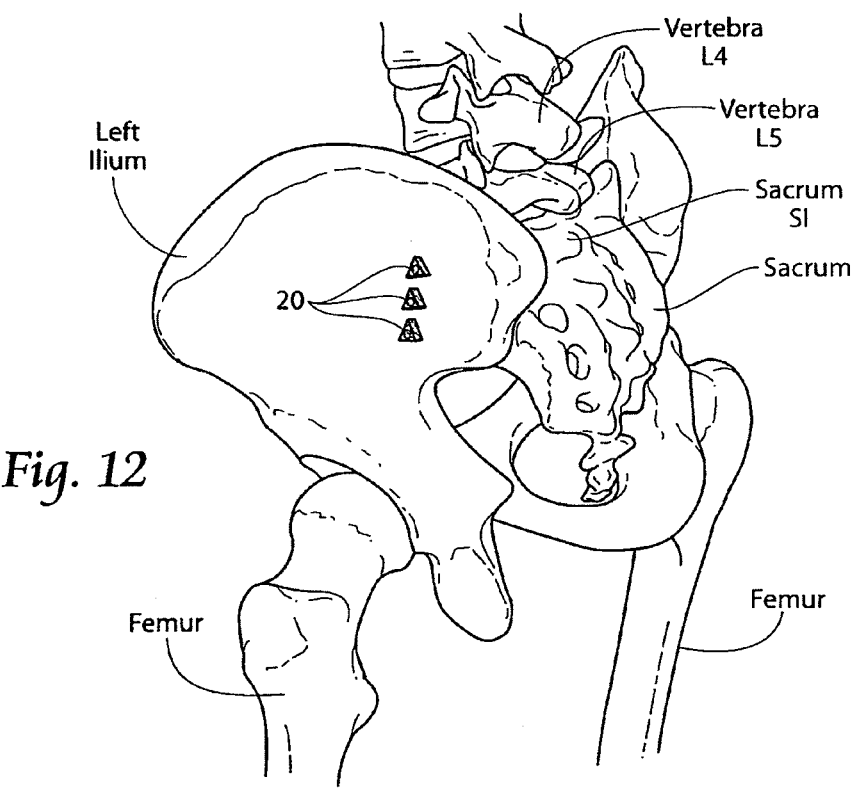
Figure 13A:
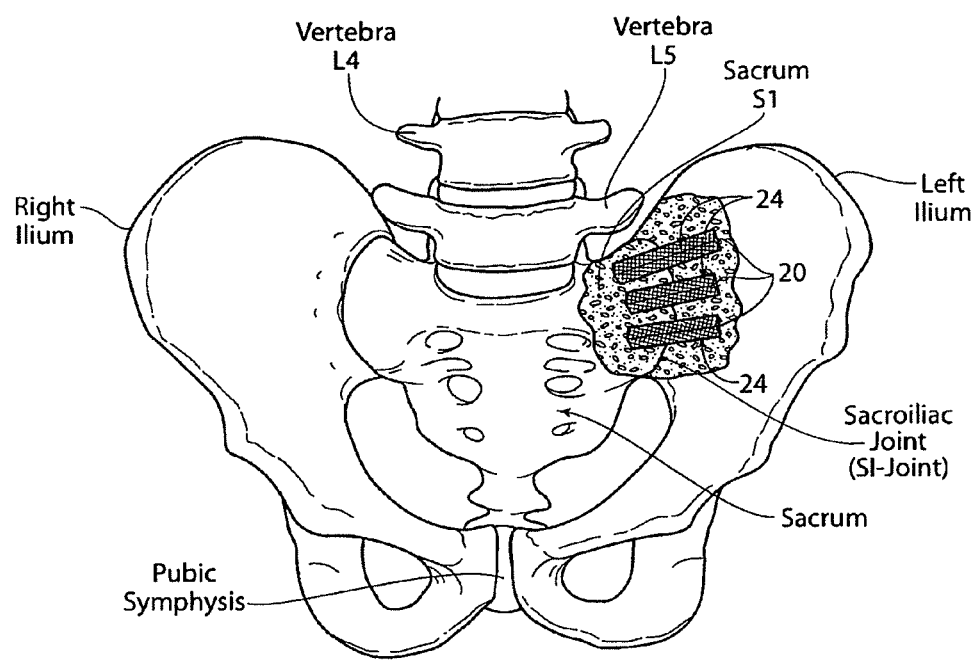
Figure 13B:
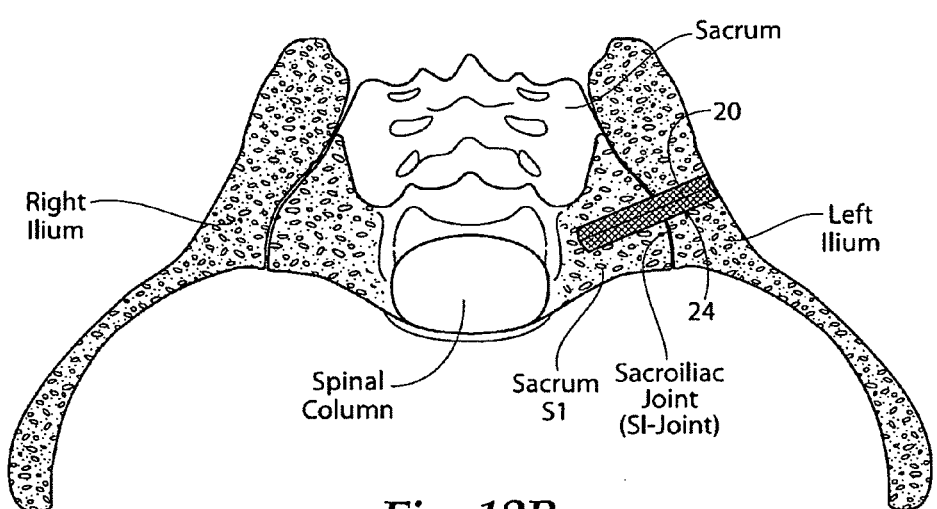

As shown in FIGS. 11 and 12, a triangular implant structure 20 can be now tapped (in this embodiment, without an associated compression sleeve assembly) through the soft tissue protector over the guide pin 38 through the ilium, across the SI-Joint, and into the S1, until the proximal end of the implant structure 20 is flush against the lateral wall of the ilium (see also FIGS. 13A and 13B). The guide pin 38 and soft tissue protector are withdrawn, leaving the implant structure 20 residing in the broached passageway, flush with the lateral wall of the ilium (see FIGS. 13A and 13B). In the illustrated embodiment, two additional implant structures 20 are implanted in this manner, as FIG. 12 best shows.

The implant structures 20 are sized according to the local anatomy. For the SI-Joint, representative implant structures 20 can range in size, depending upon the local anatomy, from about 35 mm to about 55 mm in length, and about 7 mm diameter. The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone using, for example, plain film x-ray, fluoroscopic x-ray, or MRI or CT scanning.

2. With Association of a Compression Stem Assembly

Figure 14:
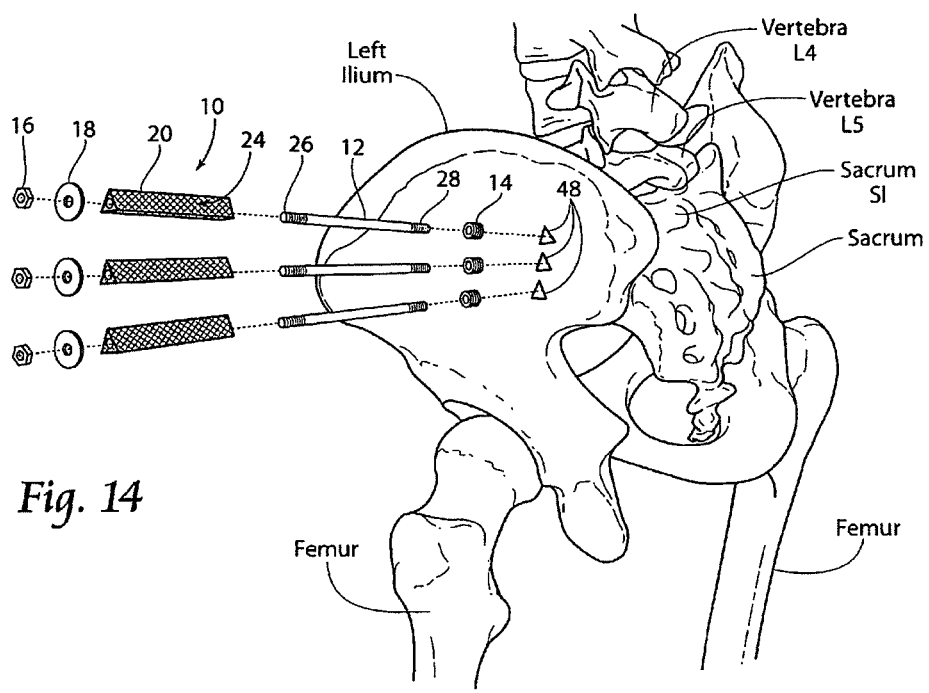
Figure 15:
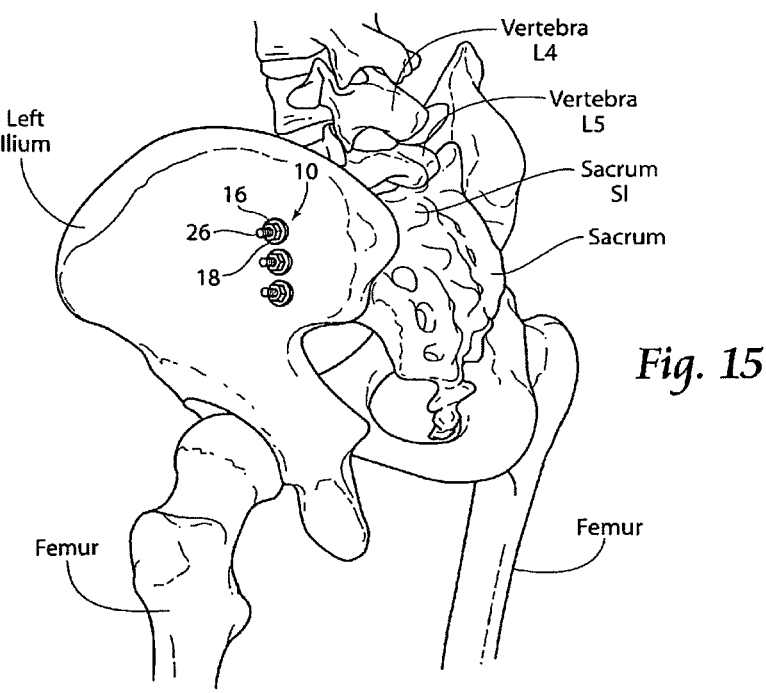
Figure 16A:
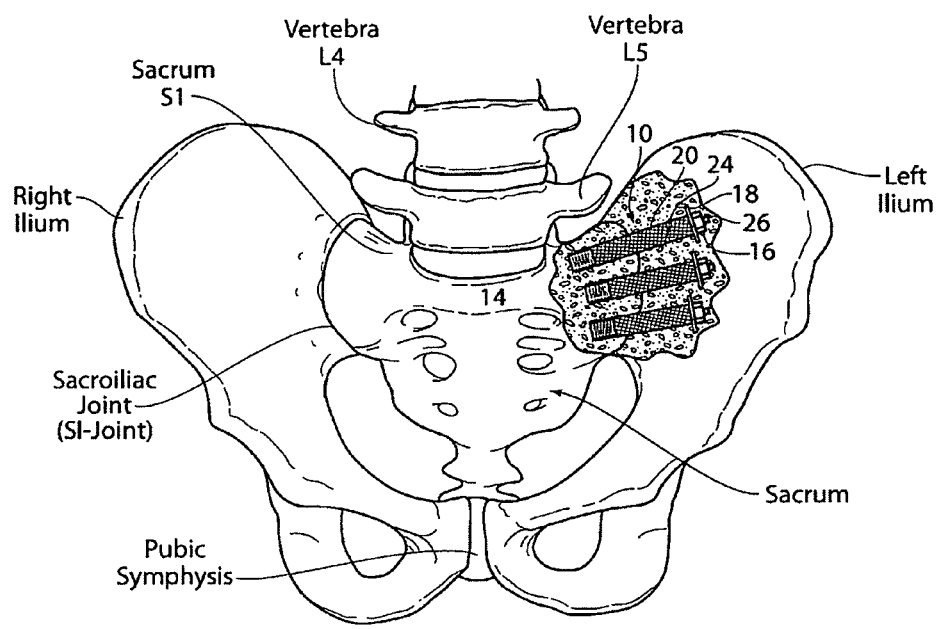

As shown in FIGS. 14 to 16A/B, the lateral approach also lends itself to the introduction of one or more implant structures 20 in association with compression stem assemblies 10, as previously described, laterally through the ilium, the SI-Joint, and into the sacrum 51. This path and resulting placement of the implant structures are best shown in FIGS. 16A and 16B. As in the embodiment shown in FIGS. 11 to 13A/B, three implant structures 20 are placed in this manner. Also, as in the embodiment shown in FIGS. 11 to 13A/B, the implant structures are triangular in cross section, but it still should be appreciated that implant structures having other cross sections, as previously described, can be used. In this embodiment of the lateral approach, the implant structure 20 is not inserted immediately following the formation of the broached bore 48. Instead, components of the compression stem assembly 10 are installed first in the broached bore 48 to receive the implant structure 20.

More particularly, following formation of the broached bore 48, as previously described, the guide pin 38 is removed, while keeping the soft tissue protector in place. The anchor screw 14 of the compression stem assembly 10 is seated in bone in the sacrum S1 beyond the terminus of the broached bore 48, in the manner generally shown in FIGS. 8E to 8G. In this arrangement, to accommodate placement of the anchor screw 14 of the compression stem assembly 10, an extent of bone in the sacrum S1 is left native and undrilled beyond the terminus of the pilot bore 42 and broached bore 48. The anchor screw 14 is advanced and buried in this extent of native and undrilled bone in the sacrum S1, as FIGS. 16A and 16B show, to be coupled to the threaded distal end 28 of the anchor body 12.

Figure 16B:
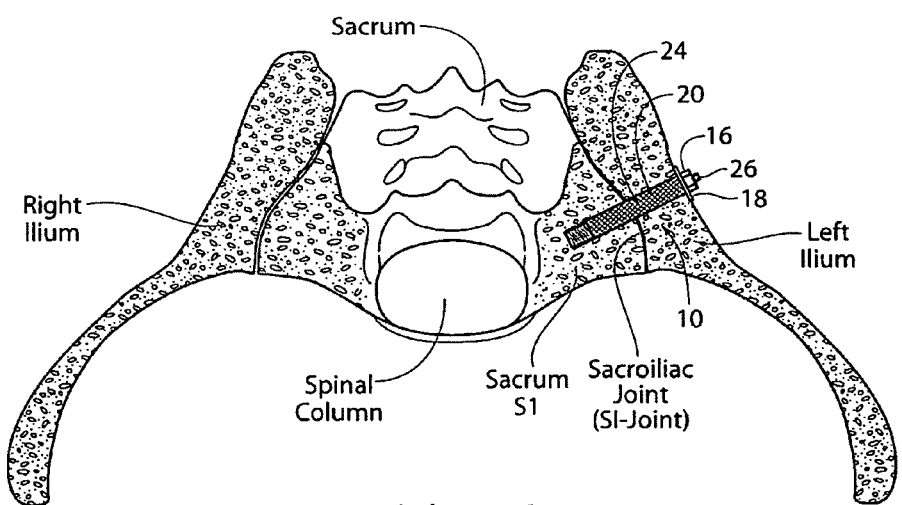
Figure 17:
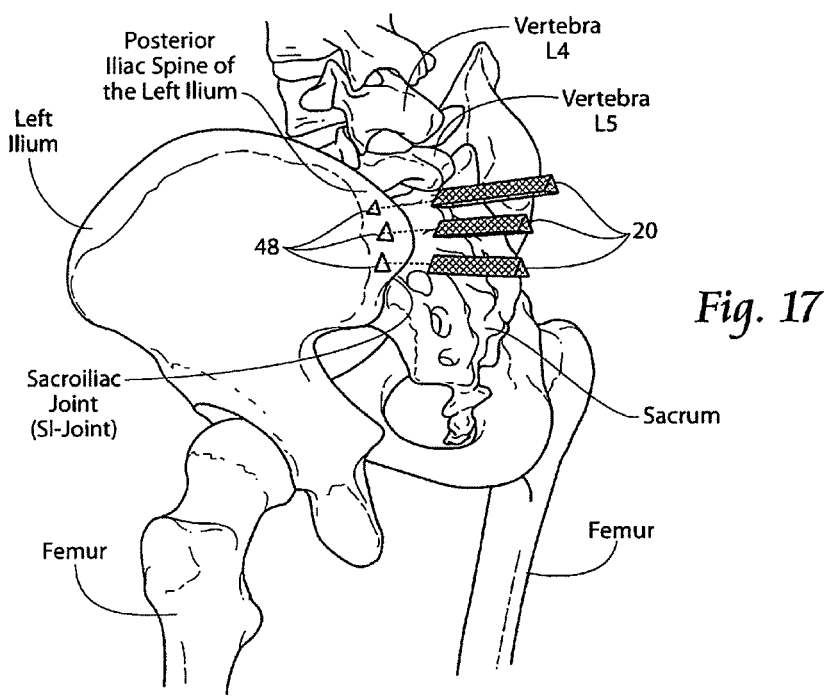

The threaded proximal end 28 of the anchor body 12 is threaded into and mated to the anchor screw 14 within the sacrum S1, as previously described and as shown in FIG. 8H, with the remainder of the anchor body 12 extending proximally through the SI-Joint and ilium, to project an exposed distance outside the lateral wall of the ilium, as FIGS. 16A and 16B show. The implant structure 20 is then placed by sliding it over the anchor body 12, until flush against the lateral wall of the ilium, as previously described and as shown in FIG. 8I. The anchor washer 18 and nut are then installed and tightened on the proximal end of the anchor body 12, as previously described and shown in FIGS. 8J to 8L, putting the assembly into compression. The resulting assembly is shown in FIGS. 15 and 16A/B.

As shown in FIGS. 14 and 15, three compression stem assemblies 10 can be installed by lateral approach across the SI-Joint. As individual compression stem assemblies are placed into compression by tightening the anchor nut 16, the implant structures of neighboring compression stem assemblies may advance to project slightly beyond the lateral wall of the ilium. If this occurs, the projecting implant structures 20 can be gently tapped further into the ilium over their respective anchor pins 12.

B. The Postero-Lateral Approach

1. Without Association of a Compression Stem Assembly

Figure 18:
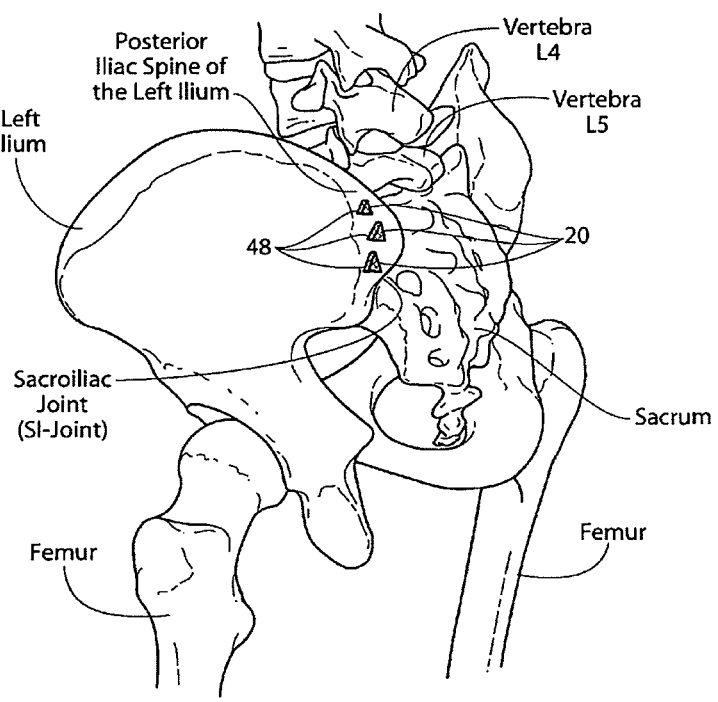
Figure 19A:
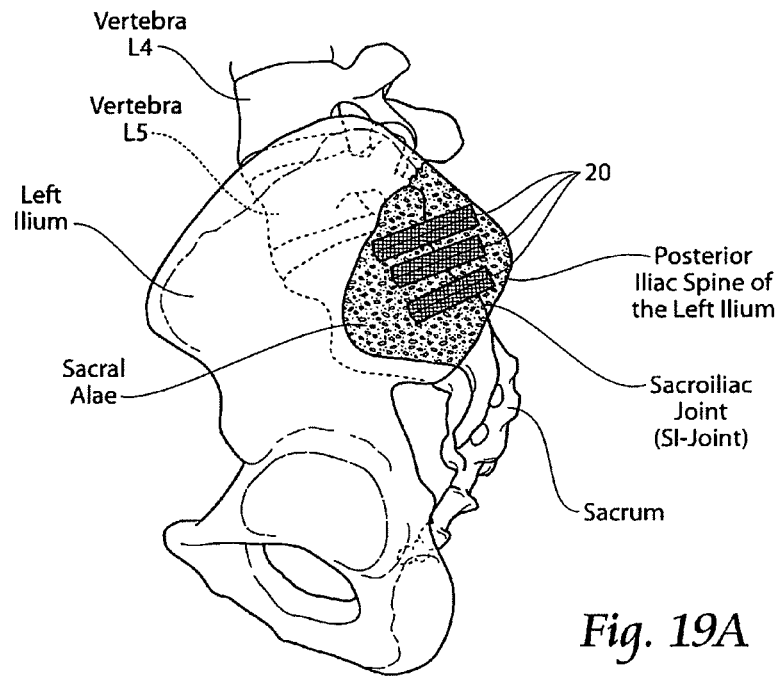
Figure 19B:
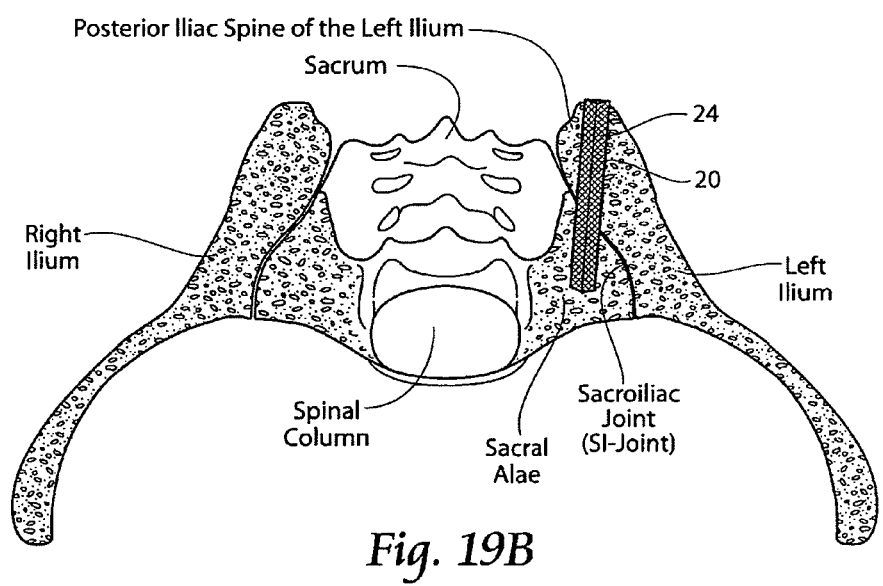

As shown in FIGS. 17 to 19A/B, one or more implant structures can be introduced (without use of a compression stem assembly 10) in a postero-lateral approach entering from the posterior iliac spine of the ilium, angling through the SI-Joint, and terminating in the sacral alae. This path and resulting placement of the implant structures 20 are best shown in FIGS. 18 and 19A/B. In the illustrated embodiment, three implant structures 20 are placed in this manner. Also in the illustrated embodiment, the implant structures 20 are triangular in cross section, but it should be appreciated that implant structures 20 of other cross sections as previously described can be used.

The postero-lateral approach involves less soft tissue disruption that the lateral approach, because there is less soft tissue overlying the entry point of the posterior iliac spine of the ilium. Introduction of the implant structure 20 from this region therefore makes possible a smaller, more mobile incision. Further, the implant structure 20 passes through more bone along the postero-lateral route than in a strictly lateral route, thereby involving more surface area of the SI-Joint and resulting in more fusion and better fixation of the SI-Joint. Employing the postero-lateral approach also makes it possible to bypass all nerve roots, including the L5 nerve root.

The set-up for a postero-lateral approach is generally the same as for a lateral approach. It desirably involves the identification of the SI-Joint segments that are to be fixated or fused (arthrodesed) using, e.g., the Faber Test, or CT-guided injection, or X-ray/MRI of SI Joint. It is desirable performed with the patient lying in a prone position (on their stomach) and is aided by lateral and anterior-posterior (A-P) c-arms. The same surgical tools are used to form the pilot bore 42 over a guide pin 38, except the path of the pilot bore 42 now starts from the posterior iliac spine of the ilium, angles through the SI-Joint, and terminates in the sacral alae. The pilot bore 42 is shaped into the desired profile using a broach, as before described (shown in FIG. 17), and the implant structure 20 is inserted into the broached bore 48 the manner shown in FIGS. 18 and 19A/B. The triangular implant structure 20 is tapped (in this embodiment, without an associated compression sleeve assembly 10) through the soft tissue protector over the guide pin 38 from the posterior iliac spine of the ilium, angling through the SI-Joint, and terminating in the sacral alae, until the proximal end of the implant structure 20 is flush against the posterior iliac spine of the ilium, as FIG. 18 shows. As shown in FIGS. 17 to 19A/B, three implant structures 20 are introduced in this manner. Because of the anatomic morphology of the bone along the postero-lateral route, it may be advisable to introduce implant structures of difference sizes, with the most superior being the longest in length, and the others being smaller in length.

2. With Association of a Compression Stem Assembly

Figure 20:
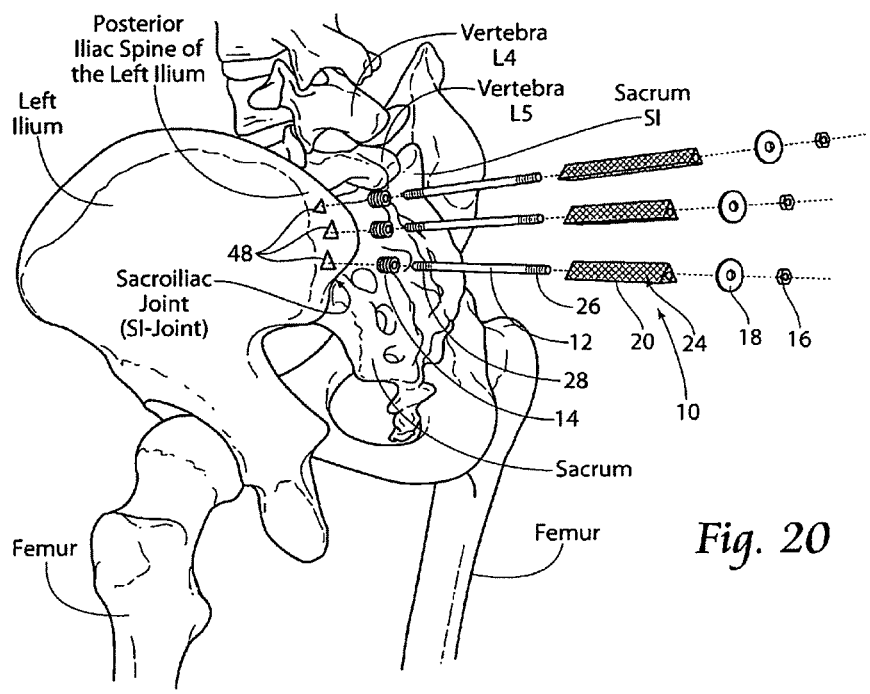
Figure 21:
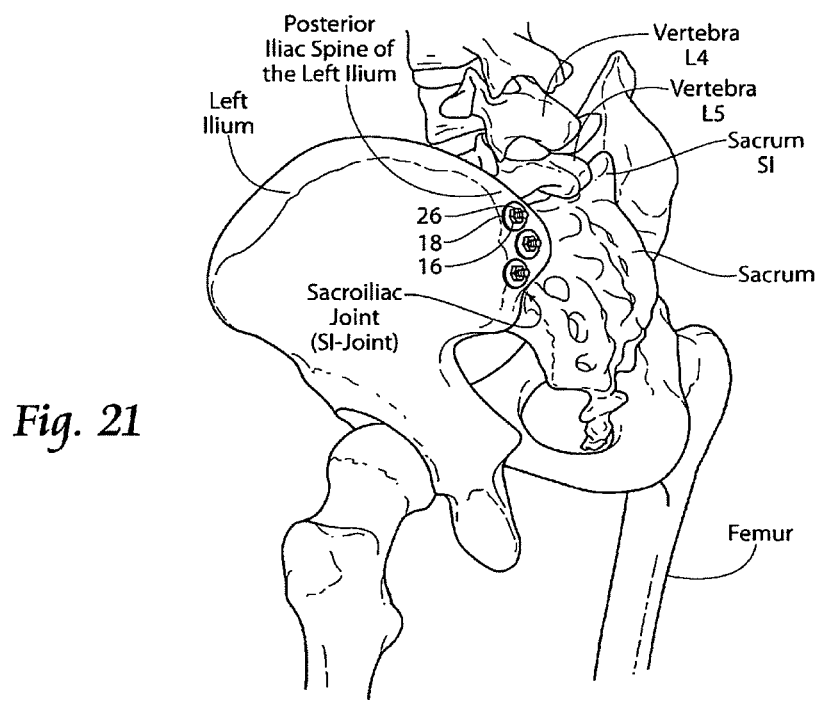
Figure 22A:
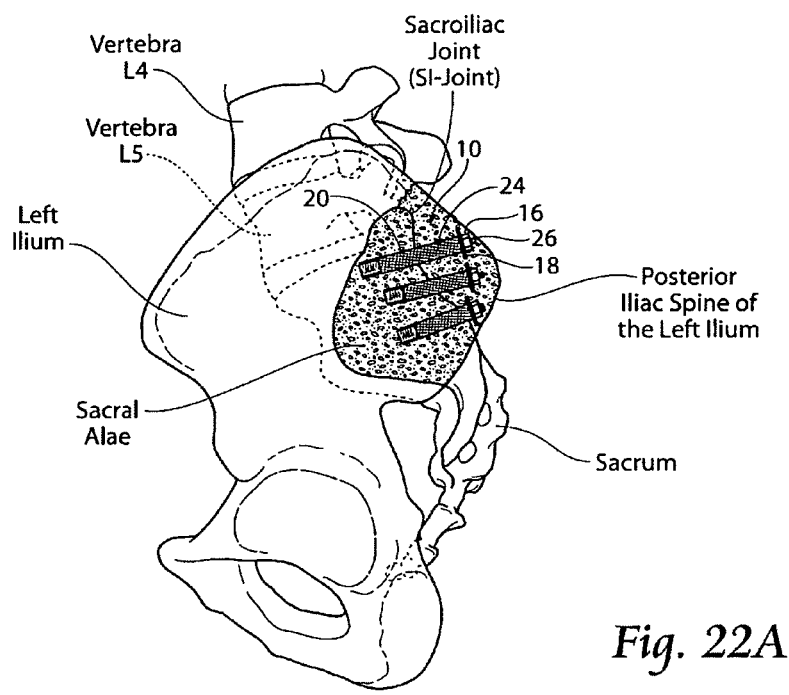

As shown in FIGS. 20 to 22A/B, the postero-lateral approach also lends itself to the introduction of one or more implant structures 20 in association with compression stem assemblies 10, as previously described, entering from the posterior iliac spine of the ilium, angling through the SI-Joint, and advancing into the sacral alae. This path and resulting placement of the implant structures 20 with compression stem assemblies 10 are best shown in FIGS. 22A/B. As in the embodiment shown in FIGS. 17 to 19A/B, three implant structures 20 are placed in this-manner. Also, as in the embodiment shown in FIGS. 17 to 19A/B, the implant structures 20 are triangular in cross section, but it still should be appreciated that implant structures 20 of other cross sections as previously described can be used. In this embodiment of the posterior-lateral approach, the implant structure 20 is not inserted immediately following the formation of the broached bore 48. Instead, components of the compression stem assembly 10 are installed in the broached bore 48 first to receive the implant structure 20, as have been previously described as is shown in FIG. 20.

As before explained, the set-up for a postero-lateral approach is generally the same as for a lateral approach. It is desirable performed with the patient lying in a prone position (on their stomach) and is aided by lateral and anterior-posterior (A-P) c-arms. The same surgical tools are used to form the pilot bore 42 over a guide pin 38 that starts from the posterior iliac spine of the ilium, angles through the SI-Joint, and terminates in the sacral alae. The pilot bore 42 is shaped into the desired profile using a broach 44, as before described (and as shown in FIG. 20). In this arrangement, to accommodate placement of the anchor screw 14 of the compression stem assembly 10, an extent of bone in the sacral alae is left native and undrilled beyond the terminus of the formed pilot bore 42 and broached bore 48. The anchor screw 14 is advanced and buried in this extent of native and undrilled bone in the sacral alae, as FIGS. 22A/B show, to be coupled to the threaded distal end 28 of the anchor body 12. Due to the morphology of the sacral alae, the anchor screw 14 may be shorter than it would be if buried in the sacrum S1 by the lateral approach.

Figure 22B:
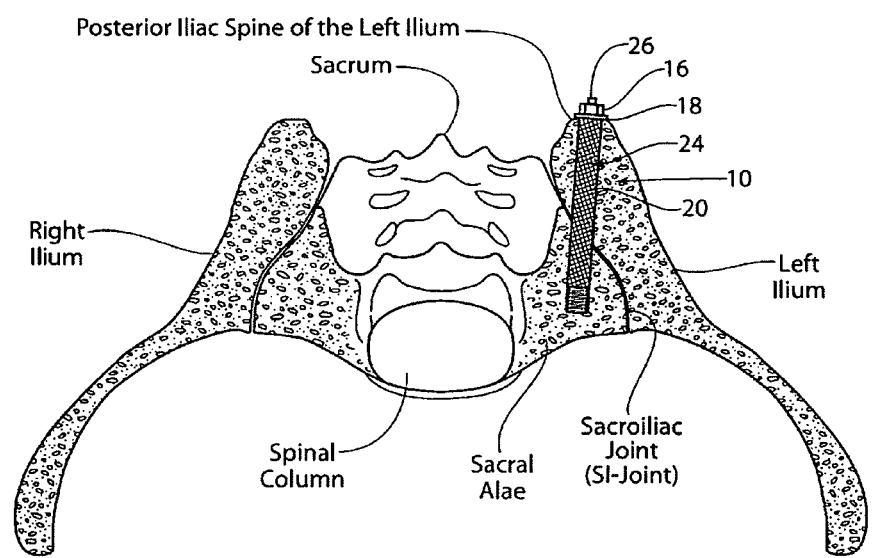

The threaded proximal end 28 of the anchor body 12 is threaded into and mated to the anchor screw 14 within the sacral alae, as previously described and as shown in FIG. 8H, with the remainder of the anchor body 12 extending proximally through the SI-Joint to project an exposed distance outside the superior iliac spine of the ilium, as FIGS. 21 to 22A/B show. The implant structure 20 is then placed by sliding it over the anchor body 12, until flush against the superior iliac spine of the ilium, as previously described and as shown in FIG. 8I. The anchor washer 18 and nut are then installed and tightened on the proximal end of the anchor body 12, as previously described and shown in FIGS. 8J to 8L, putting the assembly 10 into compression. The resulting assembly 10 is shown in FIGS. 21 and 22A/B.

As shown in FIGS. 20 and 21, three compression stem assemblies 10 can be installed by postero-lateral approach across the SI-Joint. As before explained, as individual compression stem assemblies 10 are placed into compression by tightening the anchor nut 16, the implant structures 20 of neighboring compression stem assemblies 10 may advance to project slightly beyond the superior iliac spine of the ilium. If this occurs, the projecting implant structures 20 can be gently tapped further into the superior iliac spine of the ilium over their respective anchor bodies 12.

C. Conclusion

Using either a posterior approach or a postero-lateral approach, one or more implant structures 20 can be individually inserted in a minimally invasive fashion, with or without association of compression stem assemblies 10, or combinations thereof, across the SI-Joint, as has been described. Conventional tissue access tools, obturators, cannulas, and/or drills can be used for this purpose. No joint preparation, removal of cartilage, or scraping are required before formation of the insertion path or insertion of the implant structures 20, so a minimally invasive insertion path sized approximately at or about the maximum outer diameter of the implant structures 20 need be formed.

The implant structures 20, with or without association of compression stem assemblies 10, obviate the need for autologous bone graft material, additional pedicle screws and/or rods, hollow modular anchorage screws, cannulated compression screws, threaded cages within the joint, or fracture fixation screws.

In a representative procedure, one to six, or perhaps eight, implant structures 20 might be needed, depending on the size of the patient and the size of the implant structures 20. After installation, the patient would be advised to prevent loading of the SI-Joint while fusion occurs. This could be a six to twelve week period or more, depending on the health of the patient and his or her adherence to post-op protocol.

The implant structures 20 make possible surgical techniques that are less invasive than traditional open surgery with no extensive soft tissue stripping. The lateral approach and the postero-lateral approach to the SI-Joint provide straightforward surgical approaches that complement the minimally invasive surgical techniques. The profile and design of the implant structures 20 minimize rotation and micromotion. Rigid implant structures 20 made from titanium provide immediate post-op SI Joint stability. A bony in-growth region 24 comprising a porous plasma spray coating with irregular surface supports stable bone fixation/fusion. The implant structures 20 and surgical approaches make possible the placement of larger fusion surface areas designed to maximize post-surgical weight bearing capacity and provide a biomechanically rigorous implant designed specifically to stabilize the heavily loaded SI-Joint.

III. Arthrodesis of the Sacroiliac Joint Using Other Structures

The Lateral Approach and the Postero-Lateral Approach to the SI-Joint, aided by conventional lateral and/or anterior-posterior (A-P) visualization techniques, make possible the fixation of the SI-Joint in a minimally invasive manner using other forms of fixation/fusion structures. Either approach makes possible minimal incision size, with minimal soft tissue stripping, minimal tendon irritation, less pain, reduced risk of infection and complications, and minimal blood loss.

Figure 23:
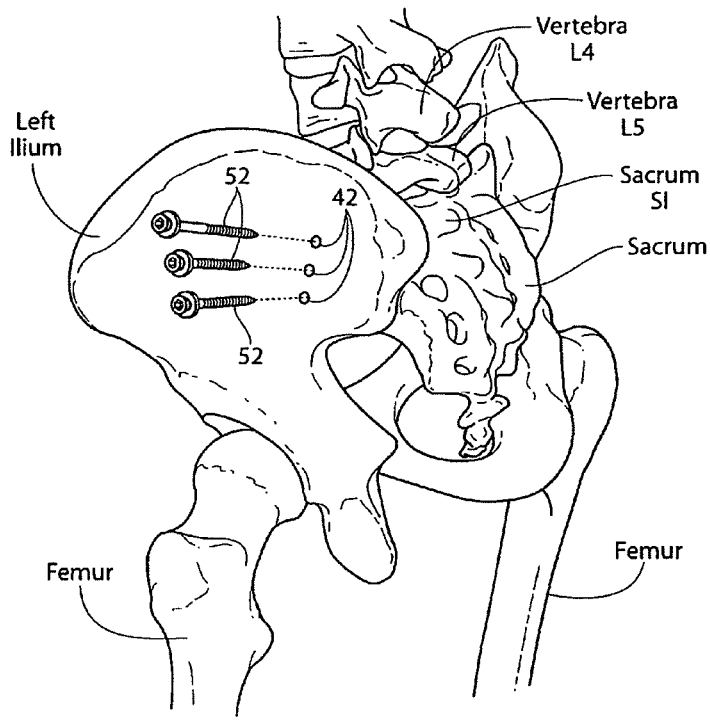
FIGS. 23 and 24A and 24B are anatomic views showing, respectively, in exploded perspective, assembled anterior view, and assembled axial section view, the implantation of a screw-like structure for the fixation of the SI-Joint using a lateral approach laterally through the ilium, the SI-Joint, and into the sacrum S1.
Figure 24A:
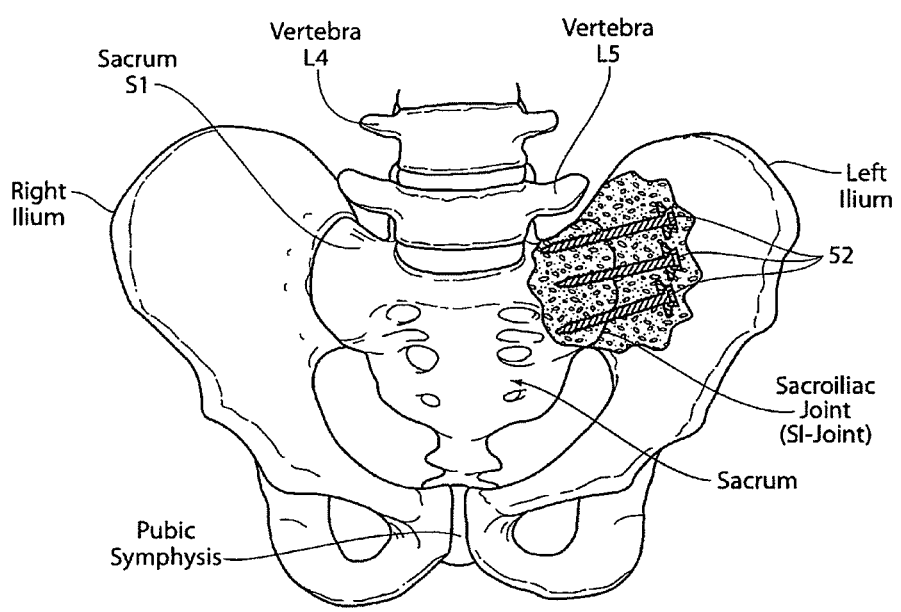
Figure 24B:
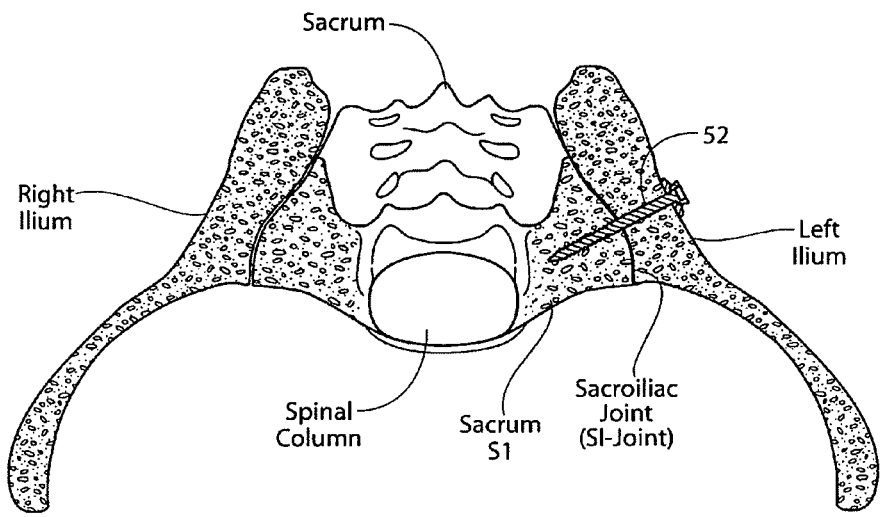

For example (see FIGS. 23 and 24A/B, one or more screw-like structures 52, e.g., a hollow modular anchorage screw, or a cannulated compression screw, or a fracture fixation screw, can be introduced using the lateral approach described herein, being placed laterally through the ilium, the SI-Joint, and into the sacrum S1. This path and resulting placement of the screw-like structures 52 are shown in FIGS. 23 and 24A/B. Desirably, the screw-like structure carry a bony in-growth material or a bony through-growth configuration, as described, as well as being sized and configured to resist rotation after implantation.

Figure 25:
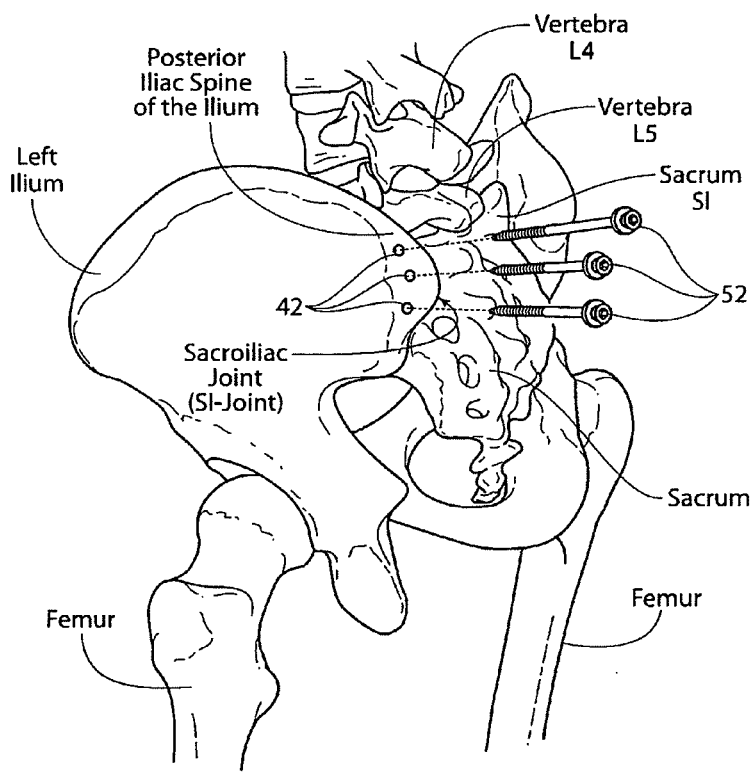
FIGS. 25 and 26A and 26B are anatomic views showing, respectively, in exploded perspective, assembled lateral view, and assembled axial section view, the implantation of a screw-like structure for the fixation of the SI-Joint using a postero-lateral approach entering from the posterior iliac spine of the ilium, angling through the SI-Joint, and terminating in the sacral alae.
Figure 26A:
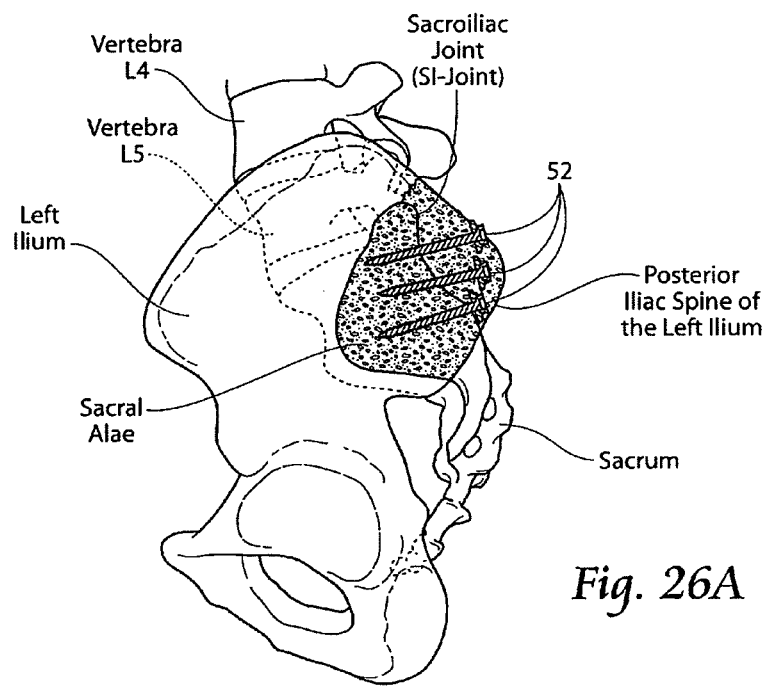
Figure 26B:
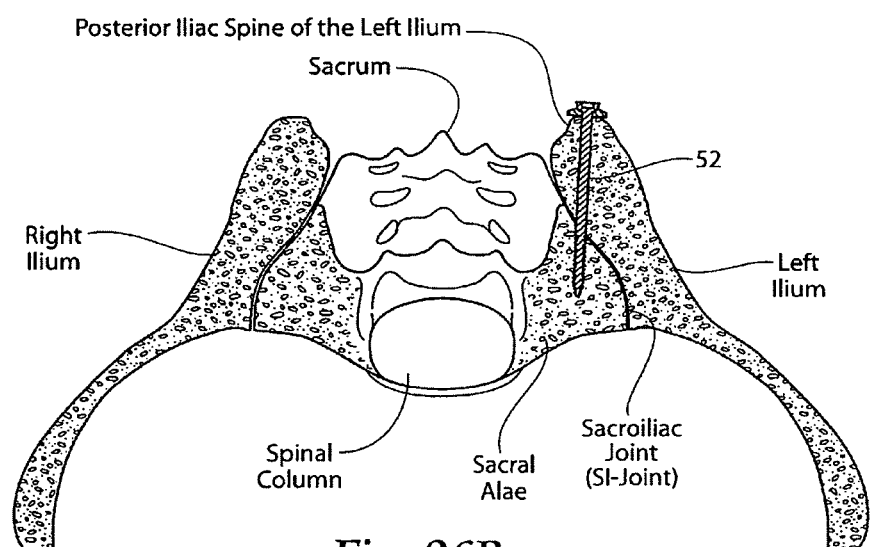

Likewise, one or more of the screw-like structures 52 can be introduced using the postero-lateral approach described herein, entering from the posterior iliac spine of the ilium, angling through the SI-Joint, and terminating in the sacral alae. This path and resulting placement of the screw-like structure are shown in FIGS. 25 and 26A/B. Desirably, the screw-like structures 52 carry a bony in-growth material or a bony through-growth configuration, as described, as well as being sized and configured to resist rotation after implantation, as before described.

Figure 27:
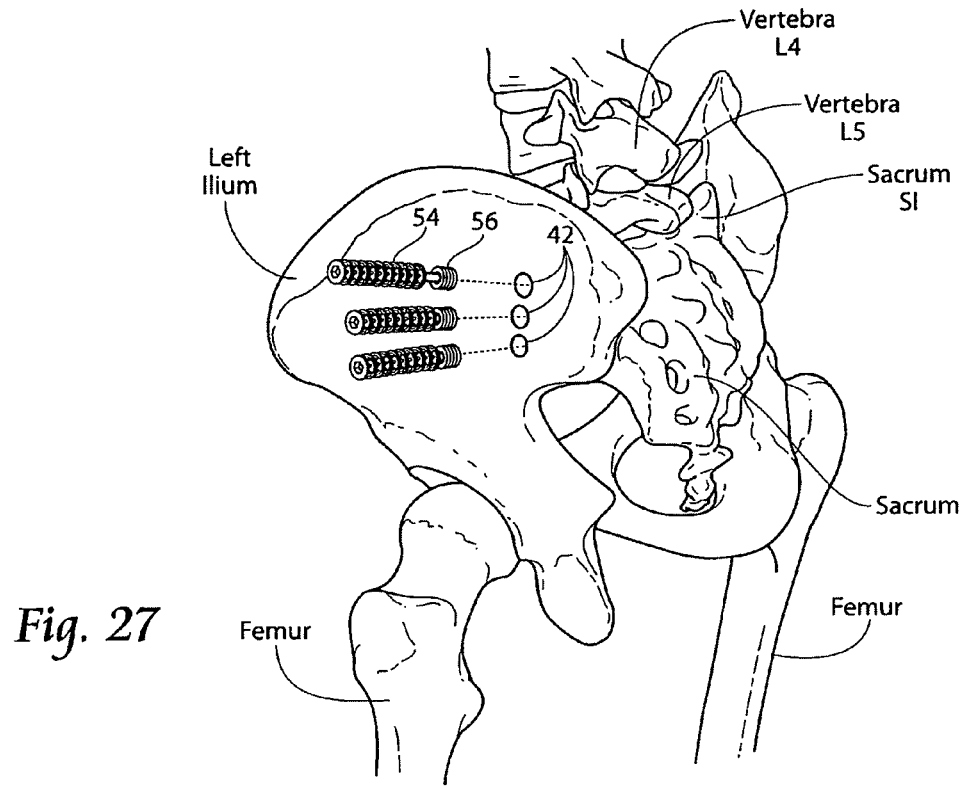
FIGS. 27 and 28A and 28B are anatomic views showing, respectively, in exploded perspective, assembled anterior view, and assembled axial section view, the implantation of a fusion cage structure for the fixation of the SI-Joint using a lateral approach laterally through the ilium, the SI-Joint, and into the sacrum S1.
Figure 28A:
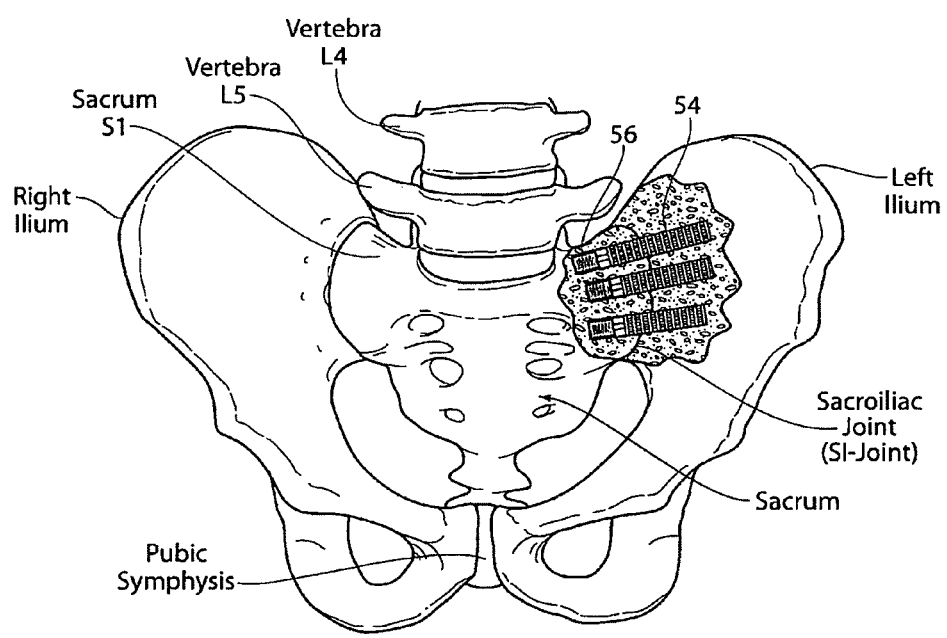
Figure 28B:
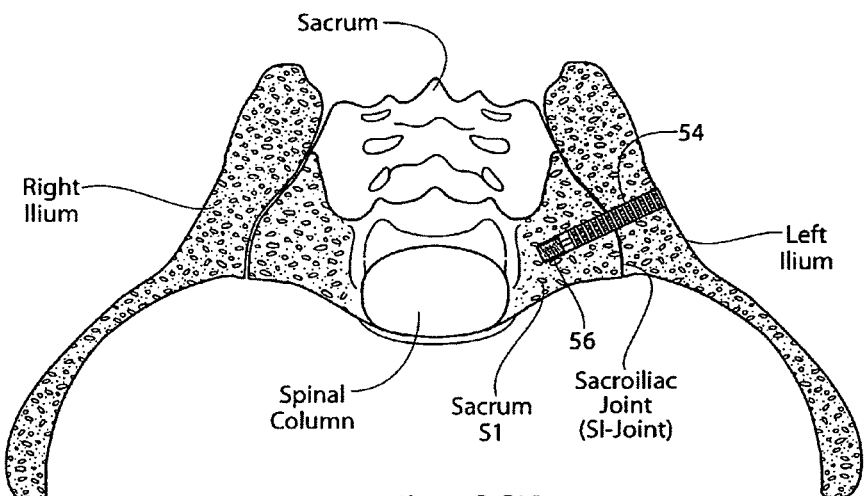

As another example, one or more fusion cage structures 54 containing bone graft material can be introduced using the lateral approach described herein, being placed laterally through the ilium, the SI-Joint, and into the sacrum S1. This path and resulting placement of the fusion cage structures 54 are shown in FIGS. 27 and 28A/B. Such a structure 54 may include an anchor screw component 56, to be seated in the sacrum S1, as shown in FIGS. 27 and 28A/B.

Figure 29:
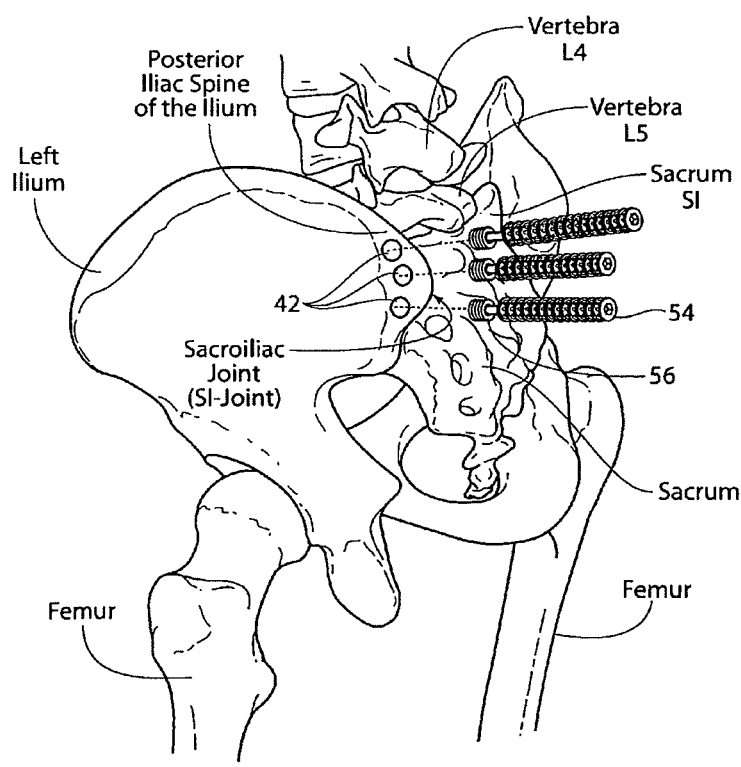
FIGS. 29 and 30A and 30B are anatomic views showing, respectively, in exploded perspective, assembled lateral view, and assembled axial section view, the implantation of a fusion cage structure for the fixation of the SI-Joint using a postero-lateral approach entering from the posterior iliac spine of the ilium, angling through the SI-Joint, and terminating in the sacral alae.
Figure 30A:
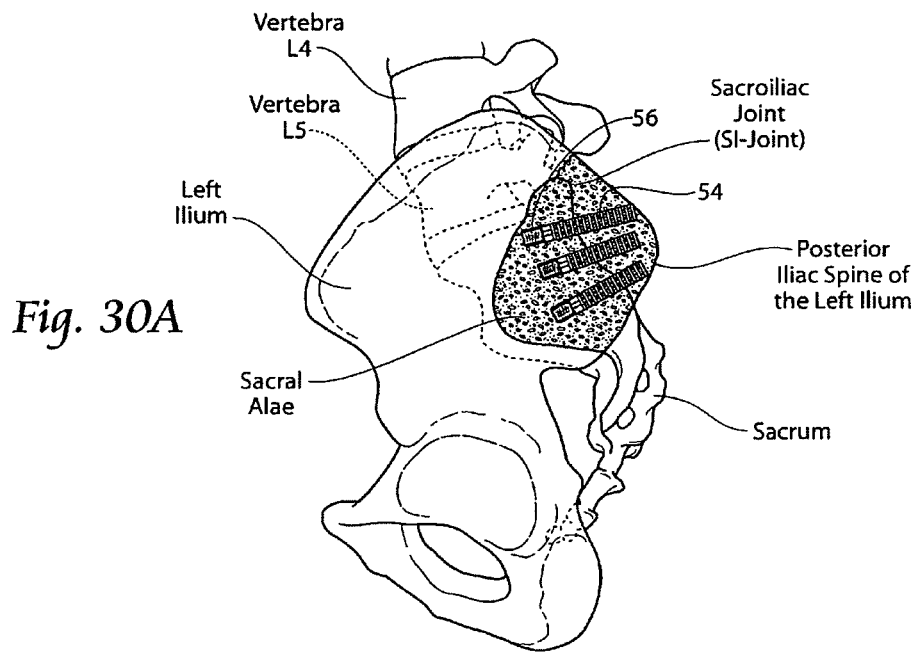
Figure 30B:
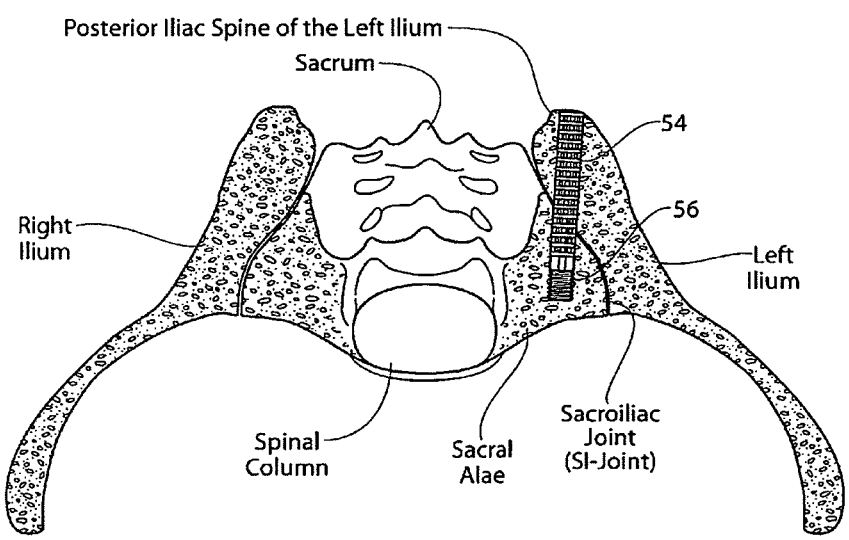

Likewise, one or more of the fusion cage structures 54 can be introduced using the postero-lateral approach described herein, entering from the posterior iliac spine of the ilium, angling through the SI-Joint, and terminating in the sacral alae. This path and resulting placement of the fusion cage structures 54 are shown in FIGS. 29 and 30A/B. Such a structure 54 may include an anchor screw component 56, to be seated in the sacral alae, as shown in FIGS. 27 and 28A/B.

IV. Conclusion

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. An assembly for the fixation or fusion of bone structures comprising first and second bone segments separated by a fracture line or joint, the assembly comprising an anchor body sized and configured to be introduced into the first and second bone segments and transversely across the fracture line or joint, the anchor body having a distal end located in an interior region of the second bone segment; a proximal end located outside an exterior region of the first bone segment; and an intermediate region spanning the fracture line or joint between the first and second bone segments, a distal anchor secured to the interior region of the second bone segment and reversibly affixed to the distal end of the anchor body to anchor the distal end in the second bone segment, a proximal anchor secured to the exterior region of the first bone segment and affixed to the proximal end of the anchor body to place, in concert with the distal anchor, the anchor body in compression to compress and fixate the bone segments relative to the fracture line or joint, and an elongated implant structure having a lumen extending therethrough and configured to be disposed coaxially over the intermediate region of the anchor body and between the proximal anchor and distal anchor and transversely spanning the fracture line or joint between the bone segments, the elongated implant structure including an exterior surface region treated to provide bony in-growth or through-growth along the implant structure to accelerate the fixation or fusion of the first and second bone segments held in compression and fixated by the anchor body.

2. An assembly according to claim 1 wherein the distal anchor comprises an externally threaded screw.

3. An assembly according to claim 2 wherein the distal end of the anchor body is threaded to engage threads formed in an interior bore of the screw.

4. An assembly according to claim 1 wherein the distal anchor comprises an interference fit between the distal end of the anchor body and bone within the interior region of the second bone segment.

5. An assembly according to claim 1 wherein the distal anchor comprises an adhesive applied between the distal end of the anchor body and bone within the interior region of the second bone segment.

6. An assembly according to claim 1 wherein the distal anchor comprises a plate having bone cutting edges rotatable into engagement with bone.

7. An assembly according to claim 1 wherein the distal anchor comprises a plate rotatable into a bone-gripping position in response to rotation of the distal region of the anchor body.

8. An assembly according to claim 1 wherein the proximal anchor comprises a nut.

9. An assembly according to claim 8 wherein the proximal anchor further includes a washer between the nut and the exterior surface of the first bone segment.

10. An assembly according to claim 8 wherein the proximal end of the anchor body is threaded to engage threads formed in an interior bore of the nut.

11. An assembly according to claim 10 wherein the proximal anchor includes a washer between the nut and the exterior surface of the first bone segment.

12. An assembly according to claim 1 wherein the implant structure has a generally curvilinear cross section.

13. An assembly according to claim 1 wherein the implant structure has a generally rectilinear cross section.

14. An assembly according to claim 1 wherein the implant structure has a generally triangular cross section.

15. An assembly according to claim 1 wherein the implant structure includes a tapered region.

16. An assembly according to claim 1 wherein the implant structure includes a tapered proximal region.

17. An assembly according to claim 1 wherein the cross section of the implant structure is larger nearer the proximal anchor than near the distal anchor.

18. An assembly according to claim 1 wherein the implant structure includes exterior bone-gripping surfaces.

19. An assembly according to claim 1 wherein the bony in-growth or through-growth region of the implant structure includes a porous plasma spray coating.

20. An assembly according to claim 1 wherein the proximal anchor in concert with the distal anchor places the implant structure in compression to bring the bony in-growth or through-growth region into intimate contact with bone within the first and segments bone segments.

21. An assembly according to claim 1 wherein the anchor body comprises a cylindrical pin or rod shaped geometry.

22. A method for the fixation or fusion of bone structures comprising:
    identifying first and second bone segments separated by a fracture line or joint,
    creating an insertion path through the first bone segment, transversely through the fracture line or joint, and into the second bone segment,
    providing an anchor body sized and configured to be introduced through the insertion path into the first and second bone segments and transversely across the fracture line or joint, the anchor body having a distal end sized and configured to be located in an interior region of the second bone segment; a proximal end sized and configured to be located outside an exterior region of the first bone segment; and an intermediate region sized and configured to span the fracture line or joint between the first and second bone segments,
    providing an elongated implant structure sized and configured to be passed coaxially over the anchor body to span the fracture line or joint between the bone segments, the elongated implant structure including an exterior surface region treated to provide bony in-growth or through-growth along the implant structure,
    introducing the anchor body through the insertion path from the first bone segment, through the fracture line or joint, and into the second bone segment,
    anchoring the distal end of the anchor body in the interior region of the second bone segment,
    passing the elongated implant structure coaxially over the anchor body to transversely span the fracture line or joint between the bone segments, and
    anchoring the proximal end of the anchor body to an exterior region of the first bone segment to place, in concert with the anchored distal end, the anchor body in compression to compress and fixate the bone segments relative to the fracture line or joint, whereby the bony in-growth or through-growth region of the implant structure accelerates the fixation or fusion of the first and second bone segments held in compression and fixated by the anchor body.

23. A method according to claim 22 wherein the distal end of the anchor body is anchored in the interior region of the second bone segment by an interference fit between the distal end and the insertion path.

24. A method according to claim 22 wherein the distal end of the anchor body is anchored in the interior region of the second bone segment by an adhesive.

25. A method according to claim 22 wherein anchoring the distal end of the anchor body includes implanting an externally threaded screw in the interior region of the second bone segment, and affixing the distal end of the anchor body to the screw.

26. A method according to claim 22 wherein anchoring the proximal end of the anchor body includes threading an anchor nut to the proximal end of the anchor body.

27. A method according to claim 22 wherein anchoring the proximal end of the anchor body includes threading an anchor nut with a washer to the proximal end of the anchor body.

28. A method according to claim 22 wherein the insertion path and the implant structure have generally concentric curvilinear cross sections.

29. A method according to claim 22 wherein the insertion path and the implant structure have generally concentric rectilinear cross sections.

30. A method according to claim 22 wherein the insertion path and the implant structure have generally concentric triangular cross sections.

* * * * *